United States Patent
Fuchiwaki

(10) Patent No.: US 9,871,204 B2
(45) Date of Patent: Jan. 16, 2018

(54) MATERIAL FOR ORGANIC ELECTROLUMINESCENCE DEVICE AND ORGANIC ELECTROLUMINESCENCE DEVICE USING THE SAME

(71) Applicant: SAMSUNG DISPLAY CO., LTD., Yongin, Gyeonggi-Do (KR)

(72) Inventor: Junta Fuchiwaki, Yokohama (JP)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 232 days.

(21) Appl. No.: 14/570,394

(22) Filed: Dec. 15, 2014

(65) Prior Publication Data
US 2015/0179951 A1    Jun. 25, 2015

(30) Foreign Application Priority Data
Dec. 20, 2013   (JP) .................................. 2013-264607

(51) Int. Cl.
  *H01L 51/50* (2006.01)
  *H01L 51/00* (2006.01)
  *C07D 307/91* (2006.01)
  *C07D 333/76* (2006.01)
  (Continued)

(52) U.S. Cl.
  CPC ........ *H01L 51/0061* (2013.01); *C07D 209/86* (2013.01); *C07D 307/91* (2013.01); *C07D 333/76* (2013.01); *C09K 11/06* (2013.01); *H01L 51/0072* (2013.01); *H01L 51/0073* (2013.01); *H01L 51/0074* (2013.01);
  (Continued)

(58) Field of Classification Search
  None
  See application file for complete search history.

(56) References Cited

U.S. PATENT DOCUMENTS 8,710,493 B2    4/2014  Nishimura et al.
2012/0119197 A1*  5/2012  Nishimura ........... C07D 209/86
                                              257/40

FOREIGN PATENT DOCUMENTS

EP    2848665 A1   8/2012
JP    2006-151844  6/2006
JP    2008-021687  1/2008
(Continued)

OTHER PUBLICATIONS

Provisional double patenting rejection over claims of the above-identified application; USPTO Office action, dated Nov. 28, 2017, in U.S. Appl. No. 14/875,312.

*Primary Examiner* — Gregory Clark
(74) *Attorney, Agent, or Firm* — Lee & Morse, P.C.

(57) ABSTRACT

A material for an organic electroluminescence device is represented by the following Formula 1,

[Formula 1]

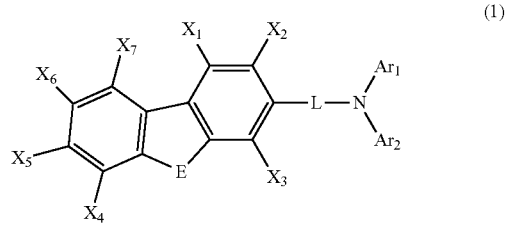

where $X_1$ to $X_7$, E, L, $Ar_1$ and $Ar_2$ are as defined in the specification.

16 Claims, 1 Drawing Sheet

(51) Int. Cl.
*C07D 209/86* (2006.01)
*C09K 11/06* (2006.01)
(52) U.S. Cl.
CPC ...... *H01L 51/0058* (2013.01); *H01L 51/0081* (2013.01); *H01L 2251/308* (2013.01)

(56) References Cited

FOREIGN PATENT DOCUMENTS

| | | |
|---|---|---|
| JP | 2012-186021 | 9/2012 |
| KR | 10-1298483 | 8/2013 |
| WO | WO-2006/128800 A1 | 12/2006 |
| WO | WO-2009/145016 A1 | 12/2009 |
| WO | WO-2010/061824 A1 | 6/2010 |
| WO | WO-2011/021520 A1 | 2/2011 |
| WO | WO-2011/040607 A1 | 4/2011 |
| WO | WO-2011/059099 A1 | 5/2011 |
| WO | WO-2011/102112 A1 | 8/2011 |
| WO | WO-2011/148909 A1 | 12/2011 |
| WO | WO-2013/036044 A2 | 3/2013 |

\* cited by examiner

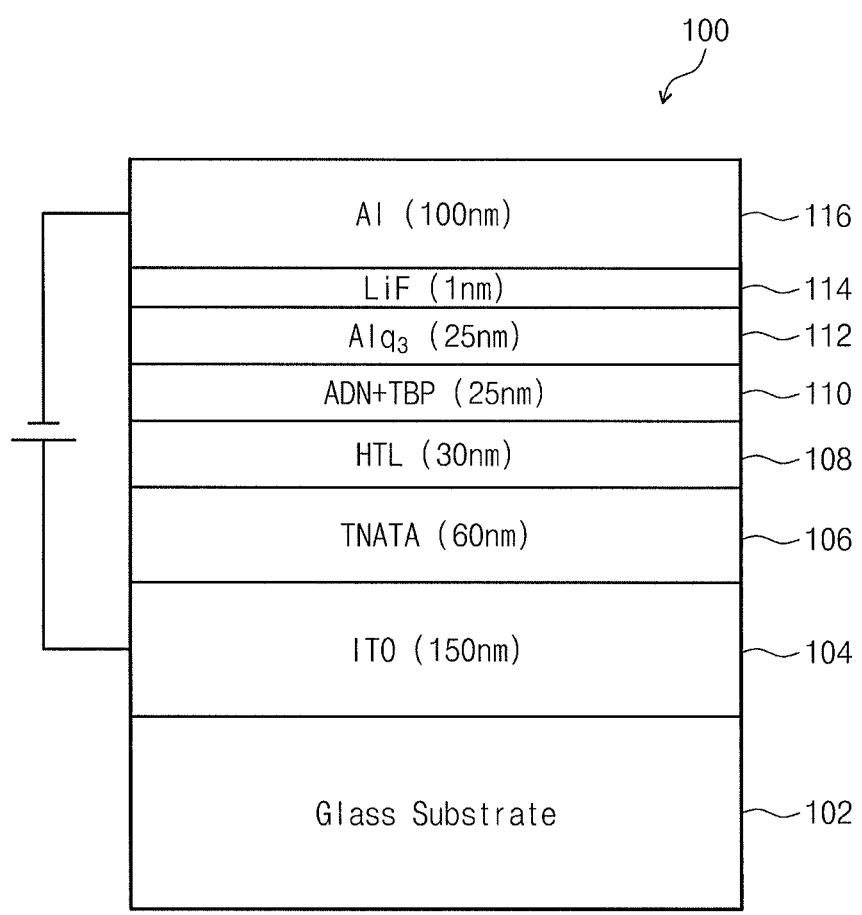

MATERIAL FOR ORGANIC ELECTROLUMINESCENCE DEVICE AND ORGANIC ELECTROLUMINESCENCE DEVICE USING THE SAME

CROSS-REFERENCE TO RELATED APPLICATION

Japanese Patent Application No. 2013-264607, filed on Dec. 20, 2013, in the Japan Patent Office, and entitled: "Material for Organic Electroluminescence Device and Organic Electroluminescence Device Using the Same," is incorporated by reference herein in its entirety.

BACKGROUND

1. Field

Embodiments relate to a material for an organic electroluminescence device and an organic electroluminescence device using the same.

2. Description of the Related Art

In recent years, organic electroluminescence (EL) displays that are one type of image displays have been actively developed. Unlike a liquid crystal display and the like, the organic EL display is so-called a self-luminescent display which recombines holes and electrons injected from an anode and a cathode in an emission layer to thus emit lights from a light-emitting material including an organic compound of the emission layer, thereby performing display.

An example of an organic electroluminescence device (organic EL device) known in the art is an organic EL device which includes an anode, a hole transport layer disposed on the anode, an emission layer disposed on the hole transport layer, an electron transport layer disposed on the emission layer, and a cathode disposed on the electron transport layer. Holes injected from the anode are injected into the emission layer via the hole transport layer. Meanwhile, electrons are injected from the cathode, and then injected into the emission layer via the electron transport layer. The holes and the electrons injected into the emission layer are recombined to generate excitons within the emission layer. The organic EL device emits light by using lights generated during the transition of the excitons to a ground state. Also, the organic EL device is not limited to the above-described configuration but may be changed in various forms.

SUMMARY

Embodiments are directed to A material for an organic electroluminescence (EL) device represented by the following Formula 1:

[Formula 1]

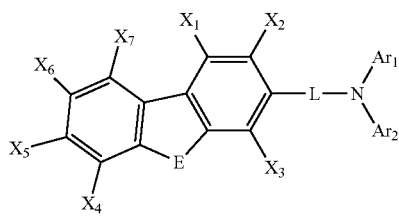

(1)

where $X_1$ to $X_7$ are independently a hydrogen atom, a deuterium atom, a halogen atom, a substituted or unsubstituted alkyl group having 1 to 15 carbon atoms, a substituted or unsubstituted aryl group having 6 to 18 ring carbon atoms, or a substituted or unsubstituted heteroaryl group having 5 to 18 ring carbon atoms, $Ar_1$ and $Ar_2$ are independently a substituted or unsubstituted aryl group having 6 to 12 ring carbon atoms, or a substituted or unsubstituted heteroaryl group having 5 to 13 ring carbon atoms, L is a divalent connecting group represented by the following Formula 2, n is 1 or 2, and E represents an oxygen atom or a sulfur atom,

[Formula 2]

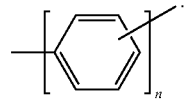

(2)

$Ar_1$ may be an aryl group having 6 to 12 ring carbon atoms.

E may be an oxygen atom.

$Ar_2$ may be one of the following Groups (3) to (5):

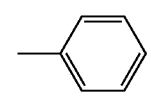

(3)

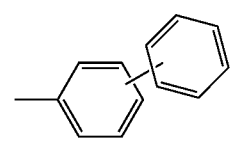

(4)

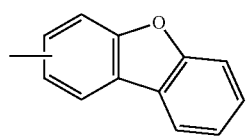

(5)

Each of $X_1$ to $X_7$ may be substituted with a hydrogen atom, a fluorine atom, a deuterium atom, an alkyl group having 1 to 15 carbon atoms, or a substituted or unsubstituted aryl group or fluoroaryl group having 6 to 18 ring carbon atoms.

The material may be one of Compounds (6) to (12):

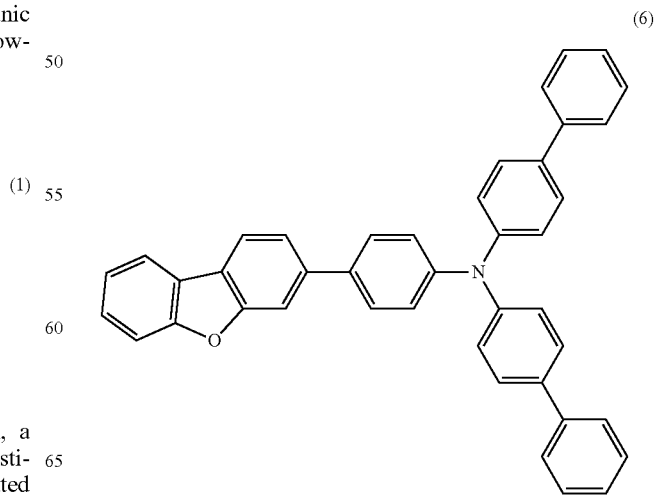

(6)

-continued (7)
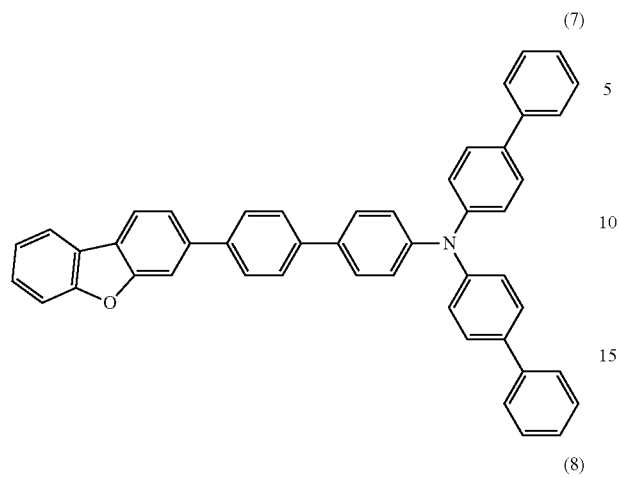

(8)
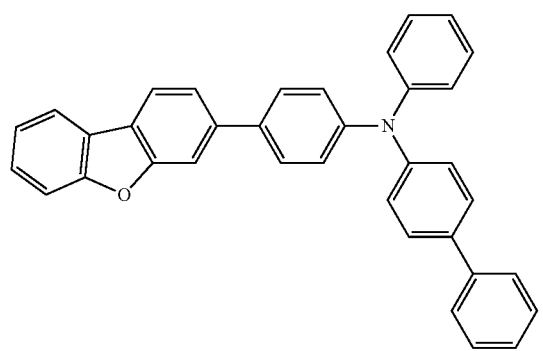

(9)

(10)
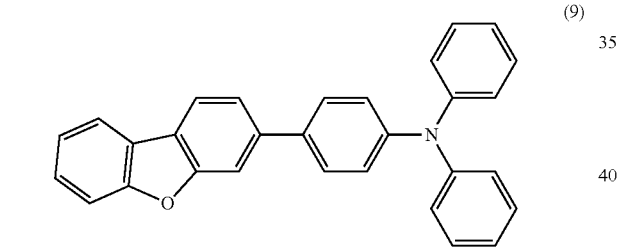

(11)
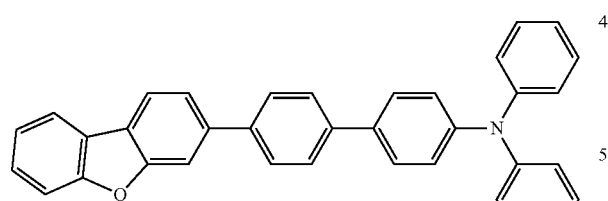

-continued

(12)
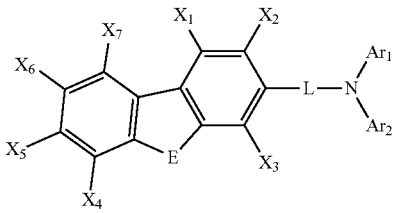

Embodiments are also directed to an organic electroluminescence (EL) device including a material for an organic EL device represented by the following Formula 6:

[Formula 6]

(6)
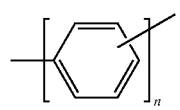

where $X_1$ to $X_7$ are independently a hydrogen atom, a deuterium atom, a halogen atom, an alkyl group having 1 to 15 carbon atoms, a substituted or unsubstituted aryl group having 6 to 18 ring carbon atoms, or a substituted or unsubstituted heteroaryl group having 5 to 18 ring carbon atoms, $Ar_1$ and $Ar_2$ are independently a substituted or unsubstituted aryl group having 6 to 12 ring carbon atoms, or a substituted or unsubstituted heteroaryl group having 5 to 13 ring carbon atoms, L is a divalent connecting group represented by the following Formula 2, n is 1 or 2, and E represents an oxygen atom or a sulfur atom,

[Formula 2]

(2)
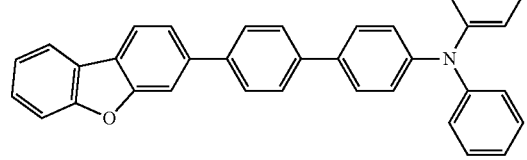

The material for an organic EL device may be included in an emission layer.

The material for an organic EL device may be included in a layer of stacked layers located between an emission layer and an anode.

$Ar_1$ may be an aryl group having 6 to 12 ring carbon atoms.

E may be an oxygen atom.

Ar₂ may be one of the following Groups (8) to (10):

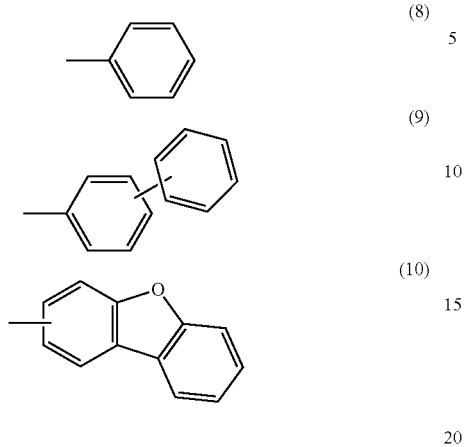

Each of $X_1$ to $X_7$ may be substituted with a hydrogen atom, a fluorine atom, a deuterium atom, an alkyl group having 1 to 15 carbon atoms, a substituted or unsubstituted aryl group or fluoroaryl group having 6 to 18 ring carbon atoms.

The material for an organic EL device may include one of the following Compounds 1 to 6:

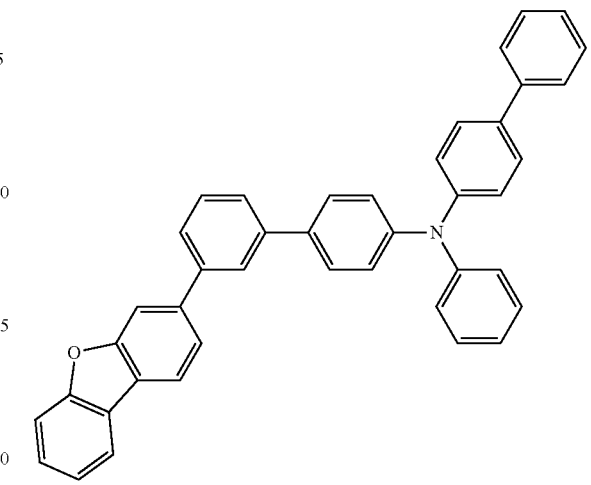

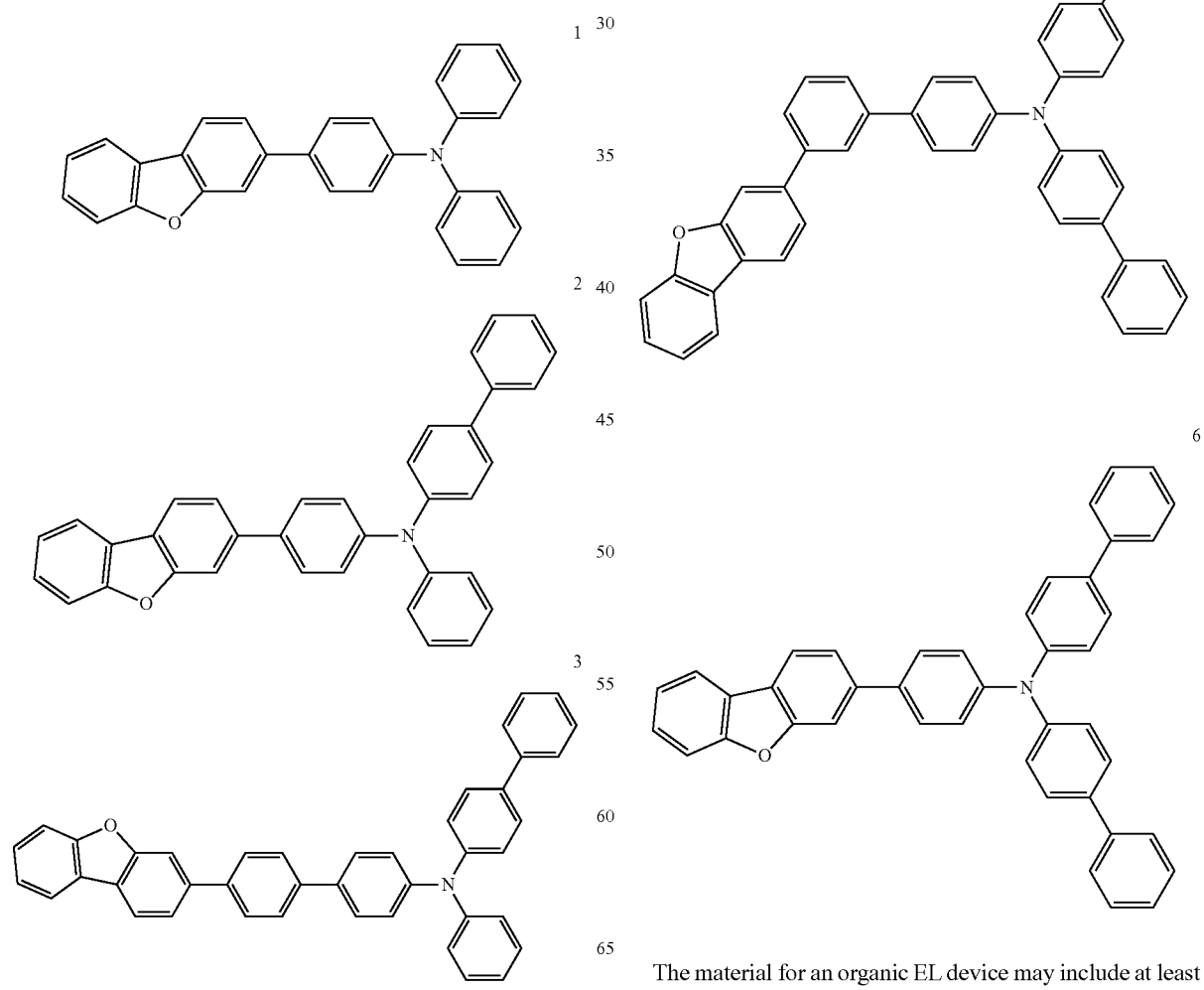

The material for an organic EL device may include at least one of Compounds 7 to 18:

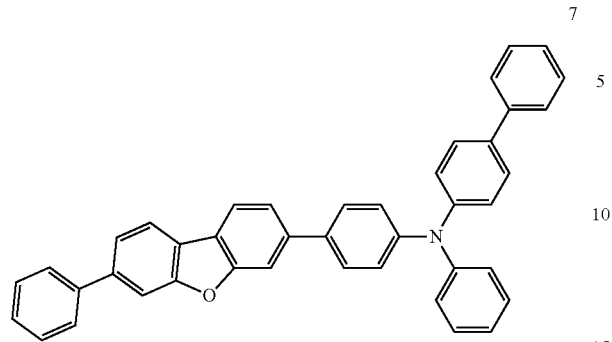
7
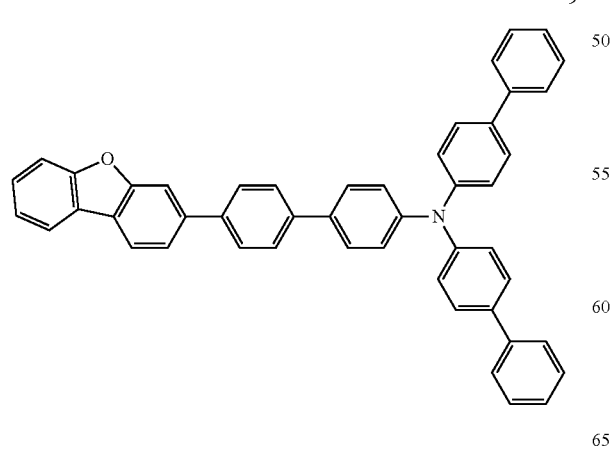
8
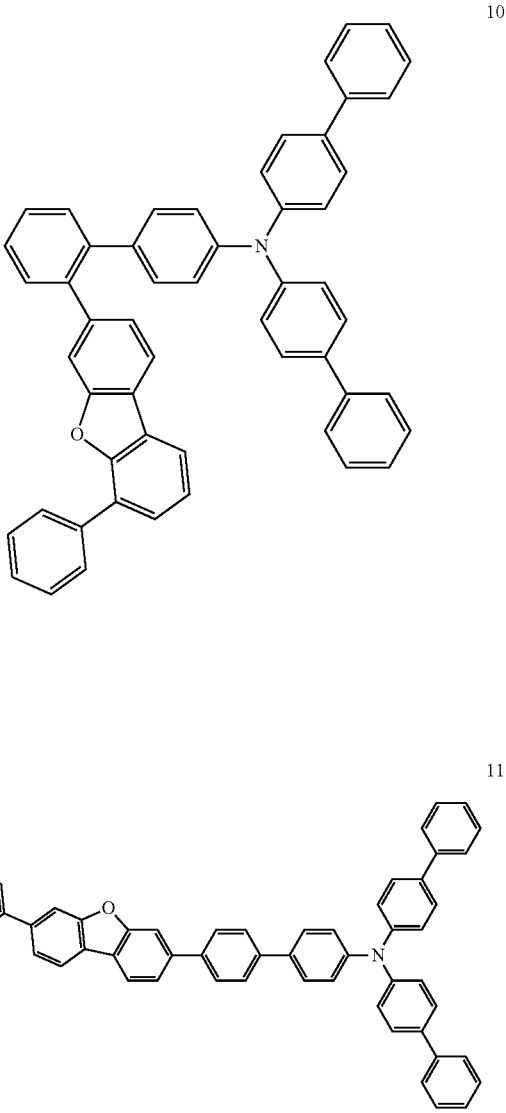
9
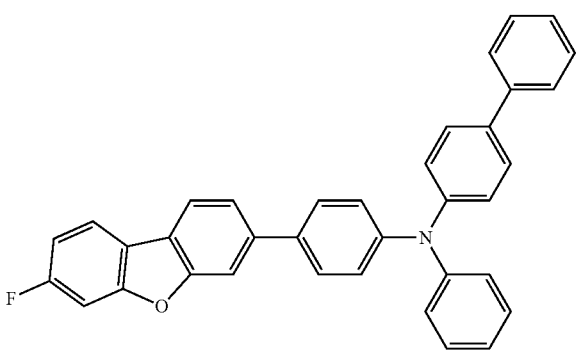
10
11
12

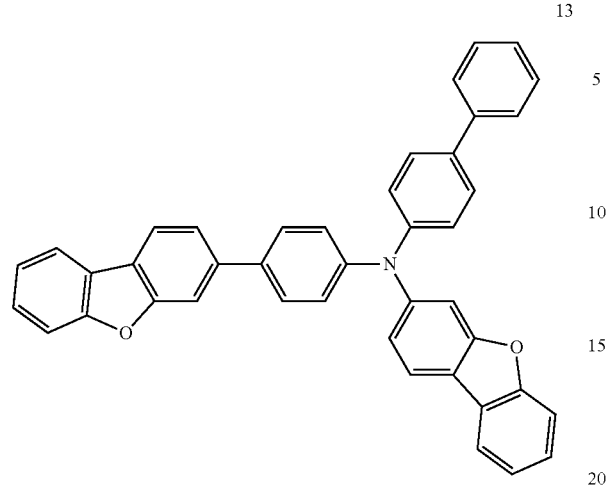
13
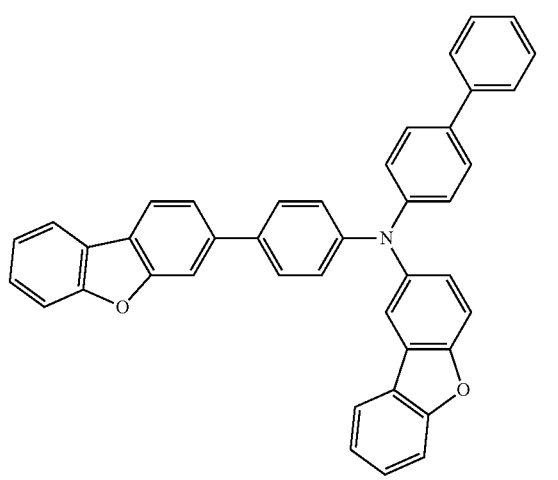
16
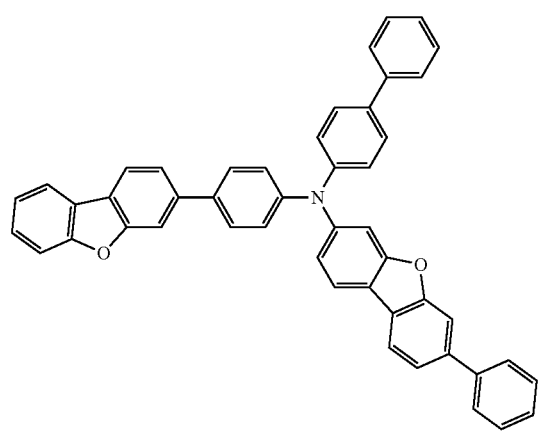
14
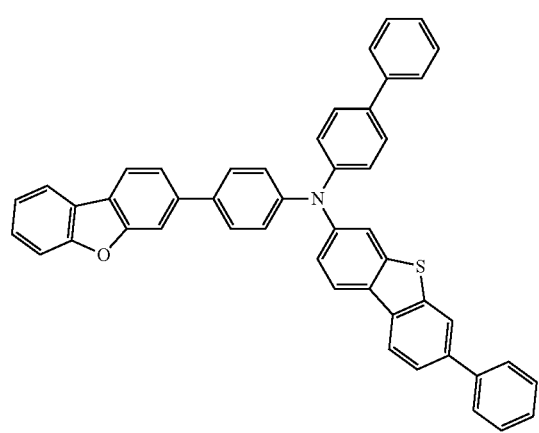
15
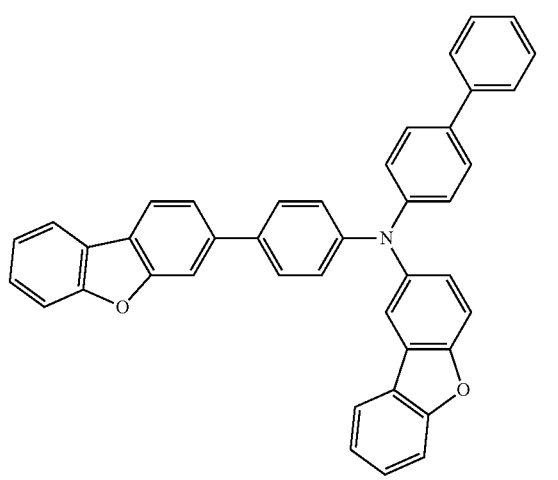
17
18
The material for an organic EL device may include at least one of Compounds 19 to 30:

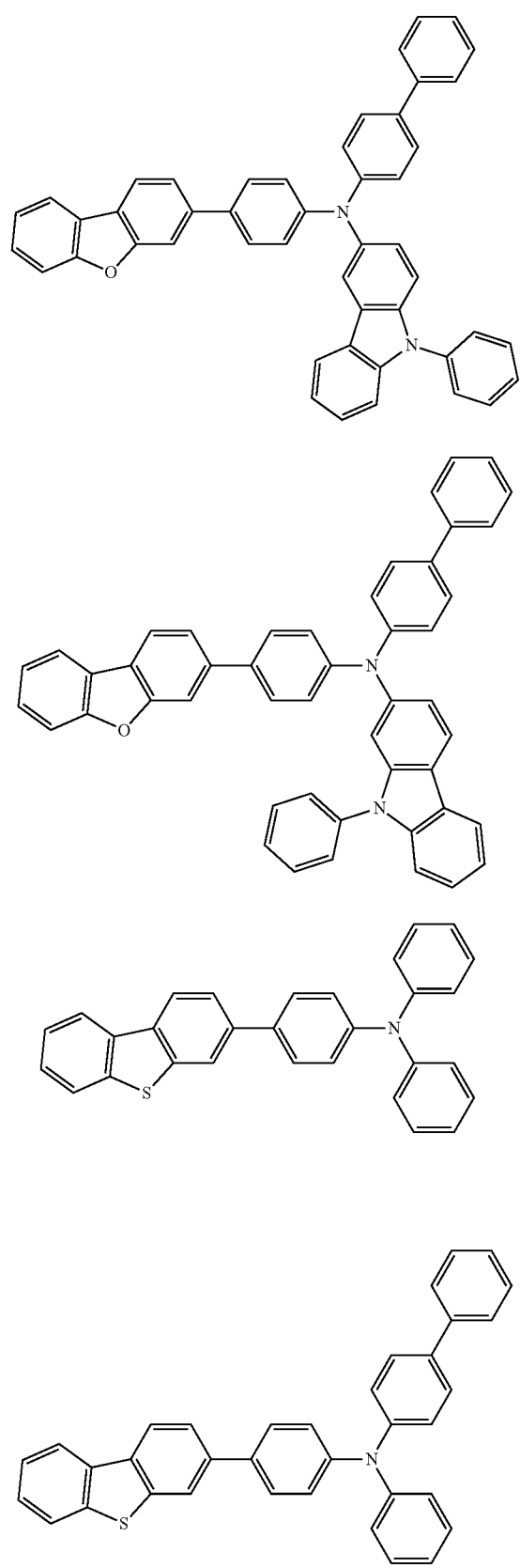
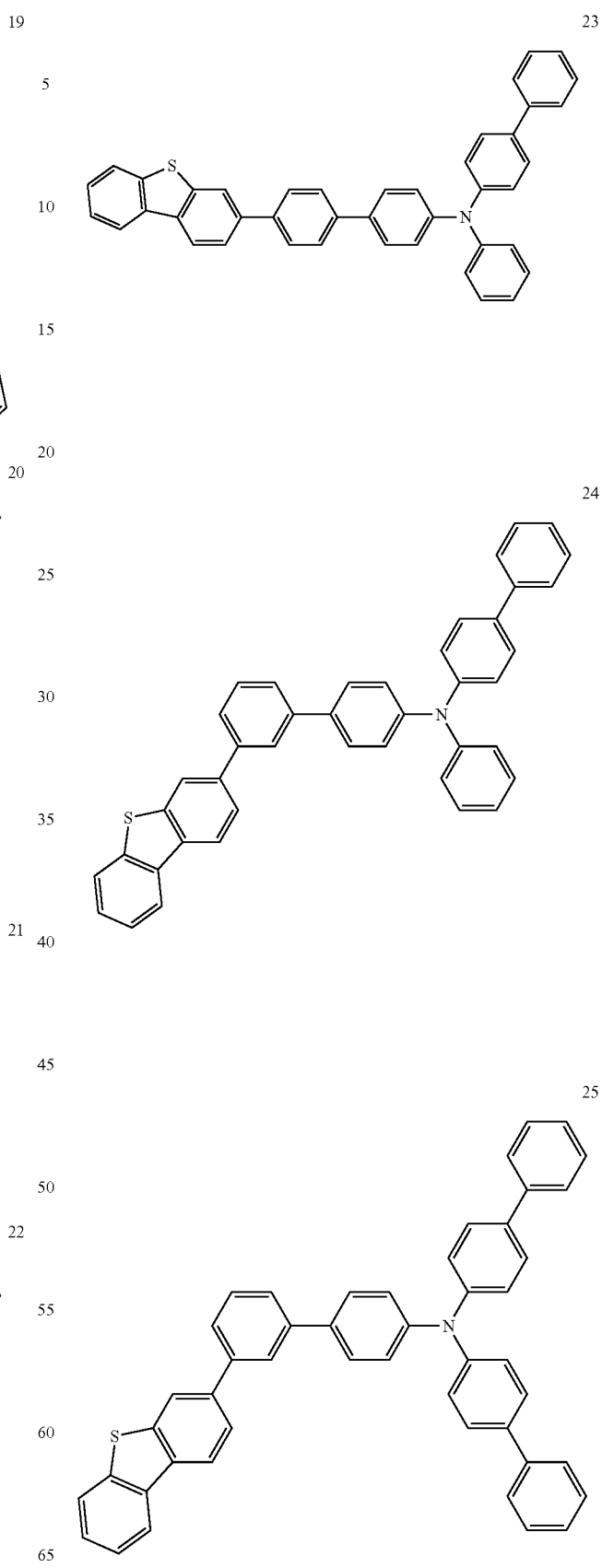

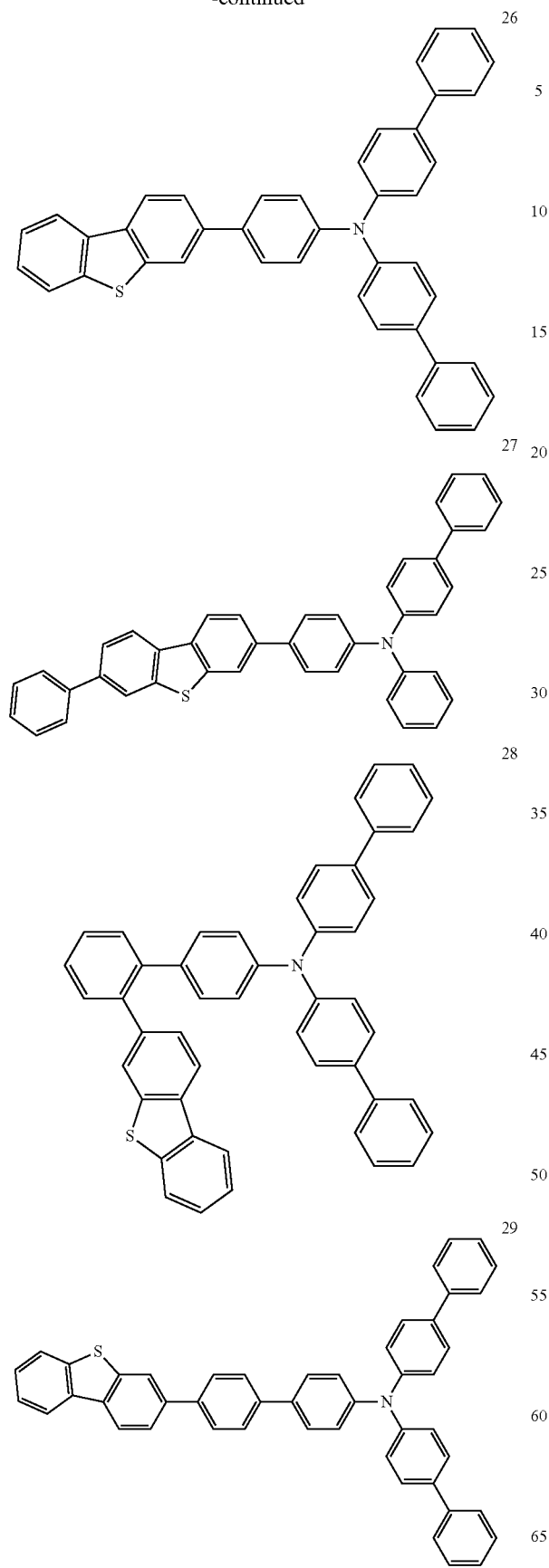
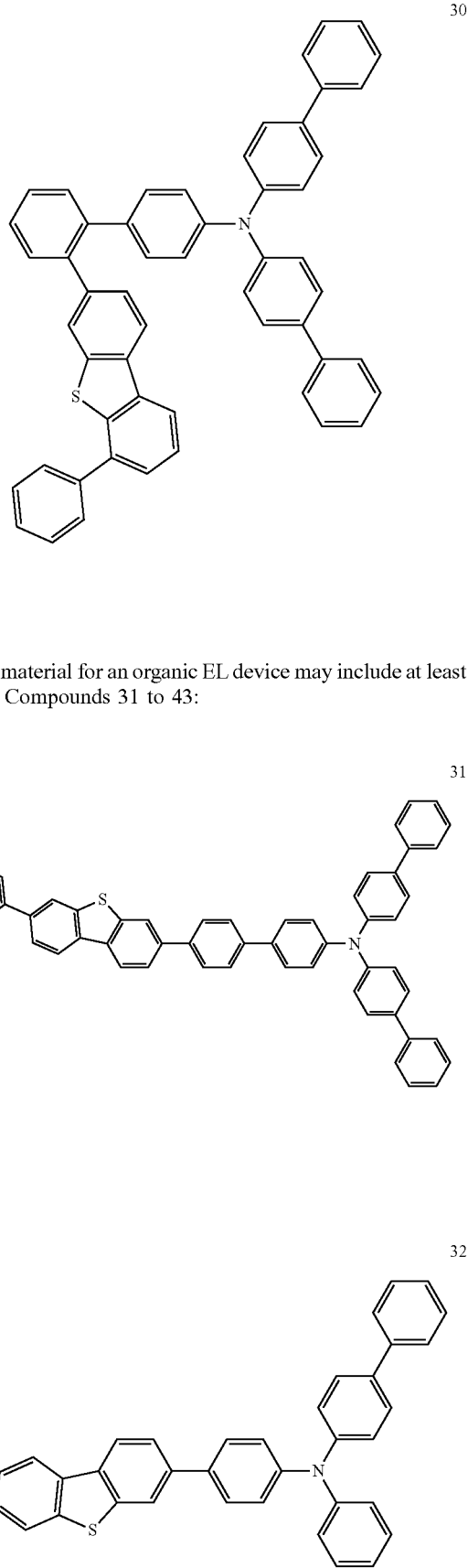
The material for an organic EL device may include at least one of Compounds 31 to 43:

33
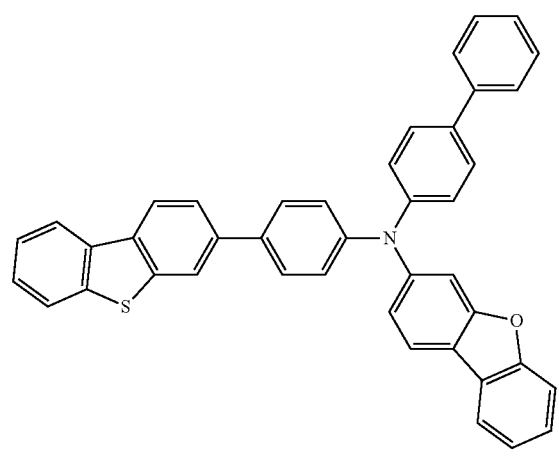
34
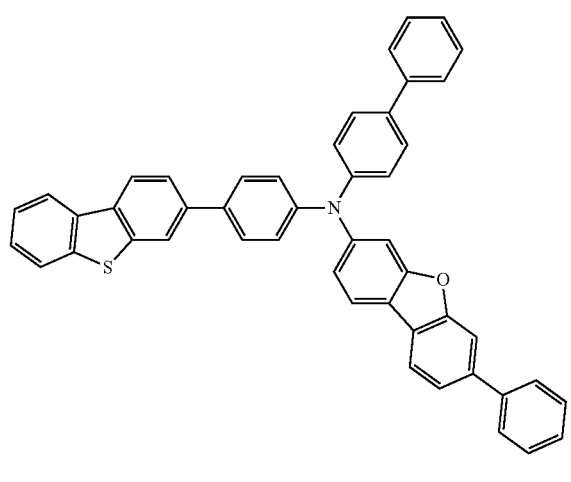
35
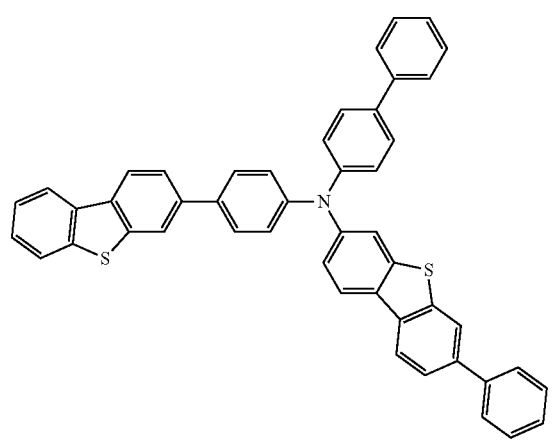
36
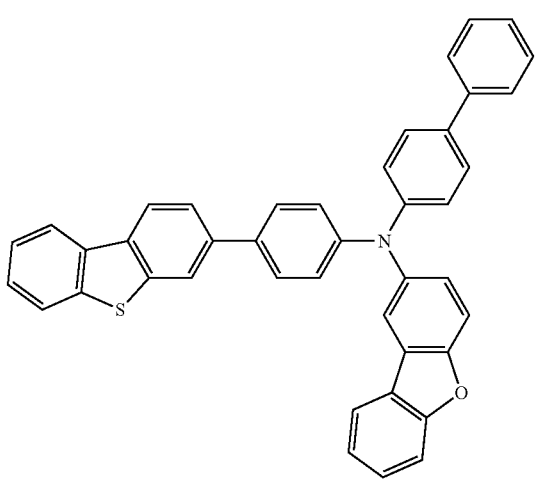
37
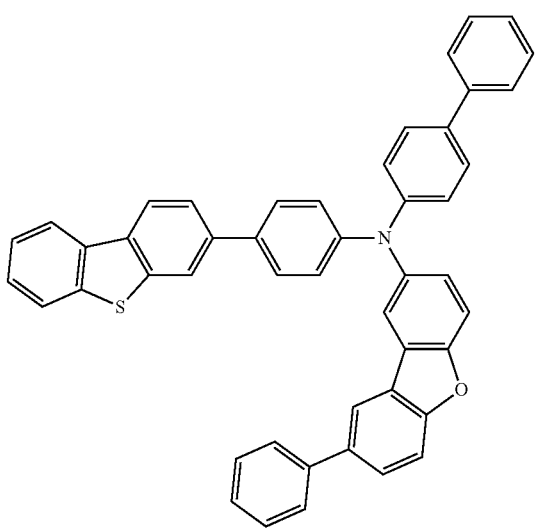
38
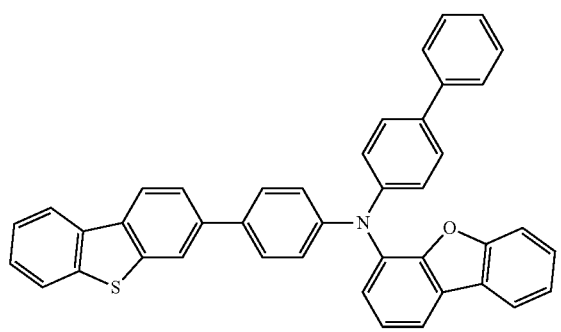

17
-continued

39

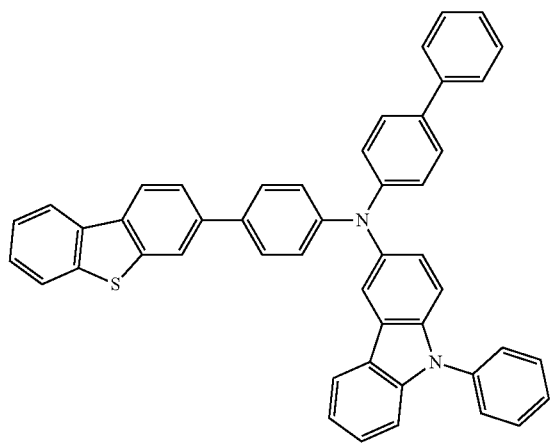

40

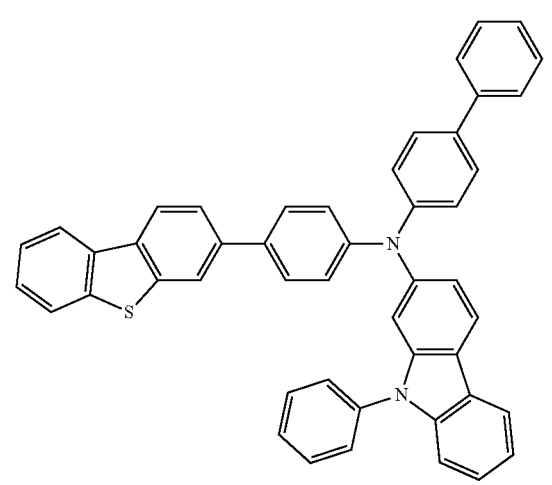

41

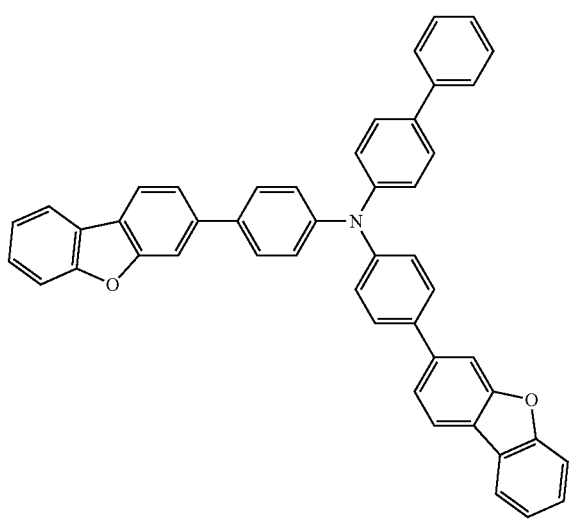

18
-continued

42

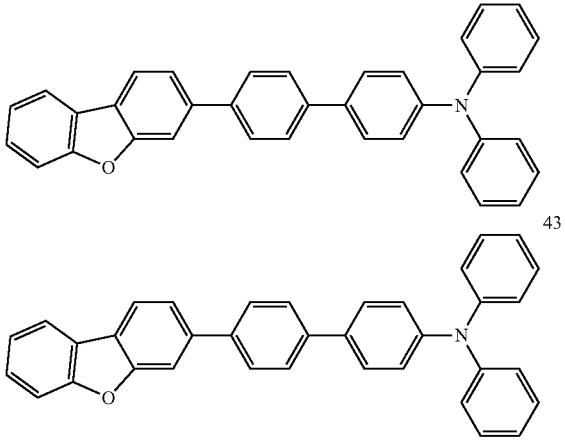

43

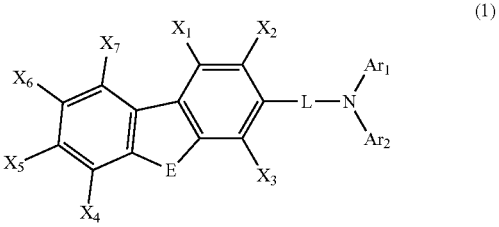

BRIEF DESCRIPTION OF THE DRAWING

Features will become apparent to those of skill in the art by describing in detail exemplary embodiments with reference to the attached drawing in which:

FIG. 1 illustrates a schematic diagram of an organic EL device 100 according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration.

A material for an organic EL device according to an embodiment may include an amine compound combined with a dibenzofuranyl group or a dibenzothiophenyl group at position 3 via a phenylene group or a biphenylene group, as represented in the following Formula 1.

[Formula 1]

$$\begin{array}{c}\text{(1)}\end{array}$$

[structure with X₁–X₇, E, L, N, Ar₁, Ar₂]

where E represents an oxygen atom or a sulfur atom. $X_1$ to $X_7$ are independently a hydrogen atom, a deuterium atom, a halogen atom, a substituted or unsubstituted alkyl group having 1 to 15 carbon atoms, a substituted or unsubstituted aryl group having 6 to 18 ring carbon atoms, or a substituted or unsubstituted heteroaryl group having 5 to 18 ring carbon atoms. Preferably, the halogen atom is fluorine.

The substituted or unsubstituted alkyl group having 1 to 15 carbon atoms, as a selection for any of $X_1$ to $X_7$, may include a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc.

The substituted or unsubstituted aryl group having 6 to 18 ring carbon atoms, as a selection for any of $X_1$ to $X_7$, may include a phenyl group, a biphenylyl group, a 1-naphthyl group, a 2-naphthyl group, a fluorophenyl group, a difluorophenyl group, a trifluorophenyl group, a tetrafluorophenyl group, a pentafluorophenyl group, a toluyl group, a nitrophenyl group, a cyanophenyl group, a fluorobiphenylyl group, a nitrobiphenylyl group, a cyanobiphenyl group, a cyanonaphthyl group, a nitronaphthyl group, a fluoronaphthyl group, a phenanthryl group, a terphenyl group, a fluoroterphenyl group, etc.

The substituted or unsubstituted heteroaryl group having 5 to 18 ring carbon atoms, as a selection for any of $X_1$ to $X_7$, may include a dibenzofuranyl group, a dibenzothiophenyl group, a pyridyl group, a chinolyl group, an isochinolyl group, a pyrazyl group, a pyrimidinyl group, a triazine group, an imidazolyl group, an acridinyl group, etc.

$Ar_1$ and $Ar_2$ may independently be a substituted or unsubstituted aryl group having 6 to 12 ring carbon atoms, or a substituted or unsubstituted heteroaryl group having 5 to 13 ring carbon atoms. Substituents of $Ar_1$ and $Ar_2$ may include, for example, a fluoro-group, a chloro-group, an alkyl group having at most 12 carbon atoms, a fluoroalkyl group having at most 12 carbon atoms, a cycloalkyl group, an acetyl group, an arylester group, an arylsulfide group, etc.

The substituted or unsubstituted aryl group having 6 to 12 ring carbon atoms, as a selection for any of $Ar_1$ and $Ar_2$, may include a phenyl group, a biphenylyl group, a 1-naphthyl group, a 2-naphthyl group, a fluorophenyl group, a difluorophenyl group, a trifluorophenyl group, a tetrafluorophenyl group, a pentafluorophenyl group, a toluyl group, a nitrophenyl group, a cyanophenyl group, a fluorobiphenylyl group, a nitrobiphenylyl group, a cyanobiphenyl group, a cyanonaphthyl group, a nitronaphthyl group, a fluoronaphthyl group, etc. For example, $Ar_1$ and $Ar_2$ may be a phenyl group, a biphenylyl group, a naphthyl group, or a fluorophenyl group. For example, $Ar_1$ and Ar2 may be a phenyl group or a biphenylyl group.

The substituted or unsubstituted heteroaryl group having 5 to 13 ring carbon atoms, as a selection for any of $Ar_1$ and $Ar_2$ may include a dibenzofuranyl group, a dibenzothiophenyl group, a pyridyl group, a chinolyl group, an isochinolyl group, a pyrazyl group, a pyrimidinyl group, a triazine group, an imidazolyl group, an acridinyl group, a carbazolyl group, etc.

L may be a divalent connecting group represented by the following Formula 6, where n is 1 or 2.

[Formula 7]

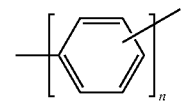

(7)

In an embodiment, L may be a phenylene group or a biphenylene group. The phenylene group or the biphenylene group may be combined with the nitrogen atom of an amine at a suitable position.

In an embodiment, the material for an organic EL device may be a compound in which E is an oxygen atom, that is, a compound including a dibenzofuranyl group. The material may be an amine compound combined with a dibenzofuranyl group with high hole tolerance and electron tolerance at position 3 via a phenylene group or a biphenylene group. Long life and high efficiency of an organic EL device may be realized when compared to an amine compound making a combination at position 2.

In an embodiment, $Ar_1$ in the material for an organic EL device may be an aryl group having 6 to 12 ring carbon atoms. The thermal decomposition of a layer of an organic EL device during forming thereof by a deposition method may be restrained by limiting the number of the carbon atom for forming a ring of $Ar_1$.

In an embodiment, $Ar_2$ in the material for an organic EL device may be represented by one of following groups (8) to (10):

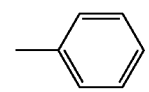

(8)

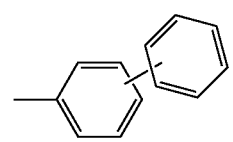

(9)

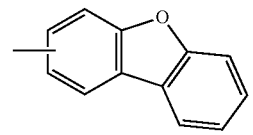

(10)

The thermal decomposition of a layer of an organic EL device during forming thereof by a deposition method may be restrained by limiting the number of the carbon atom for forming a ring of $Ar_2$.

In an embodiment $X_1$ to $X_7$ in the material for an organic EL device may be a hydrogen atom, a fluorine atom, a deuterium atom, a substituted or unsubstituted alkyl group having 1 to 15 carbon atoms, a substituted or unsubstituted aryl group or fluoroaryl group having 6 to 18 ring carbon atoms. The substituted or unsubstituted aryl group having 6 to 18 ring carbon atoms, as a selection for any of $X_1$ to $X_7$, may include a phenyl group, a biphenylyl group, a 1-naphthyl group, a 2-naphthyl group, a fluorophenyl group, a difluorophenyl group, a trifluorophenyl group, a tetrafluorophenyl group, a pentafluorophenyl group, a toluyl group, a nitrophenyl group, a cyanophenyl group, a fluorobiphenylyl group, a nitrobiphenylyl group, a cyanobiphenyl group, a cyanonaphthyl group, a nitronaphthyl group, a fluoronaphthyl group, a phenanthryl group, a terphenyl group, a fluoroterphenyl group, etc. for example, the substituted or unsubstituted aryl group may be a phenyl group or a biphenylyl group.

In the material for an organic EL device, the dibenzofuranyl group or the dibenzothiophenyl group may be combined with L at the connecting part of position 3. In a material in which a dibenzofuranyl group or a dibenzothiophenyl group is combined with L at position 2, the nitrogen atom of an amine and the oxygen atom or the sulfur atom of the dibenzofuranyl group or the dibenzothiophenyl group are disposed at para position. Thus, the reactivity of radical cations and radical anions may be high, and the realization of the long life of a device may be difficult. According to embodiments, the dibenzofuranyl group or the dibenzothiophenyl group may be combined with the connecting group at position 3. Accordingly, the stability of the compound with respect to holes and electrons may be high, and the longer life of a device may be realized.

The material for an organic EL device according to embodiments may be an amine compound combined with the dibenzofuranyl group or the dibenzothiophenyl group with high hole tolerance and electron tolerance at position 3 via the phenylene group or the biphenylene group. A longer life and higher efficiency of an organic EL device may be realized when compared to a device using an amine compound making a combination at position 2. In addition, the thermal decomposition of a layer during forming thereof by a deposition method may be restrained by controlling the number of e carbon atoms forming a ring of $Ar_1$ or $Ar_2$.

The material for an organic EL device according to an embodiment may be a material illustrated in the following structures 1 to 6.

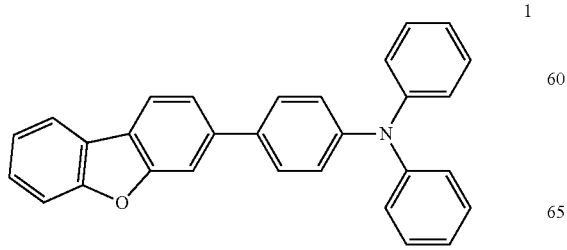

1

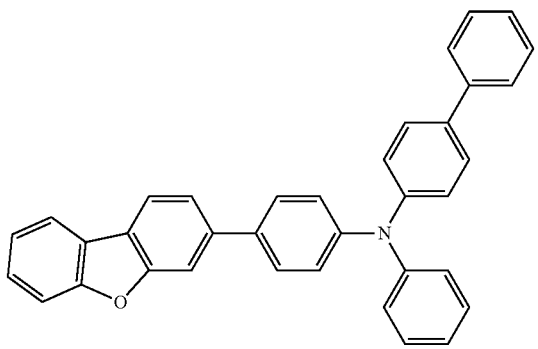

2

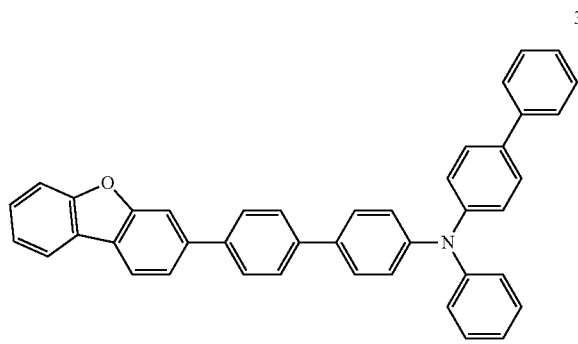

3

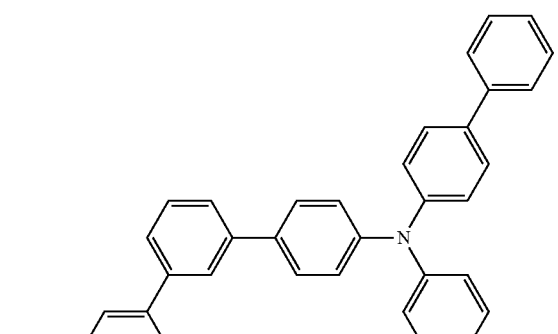

4

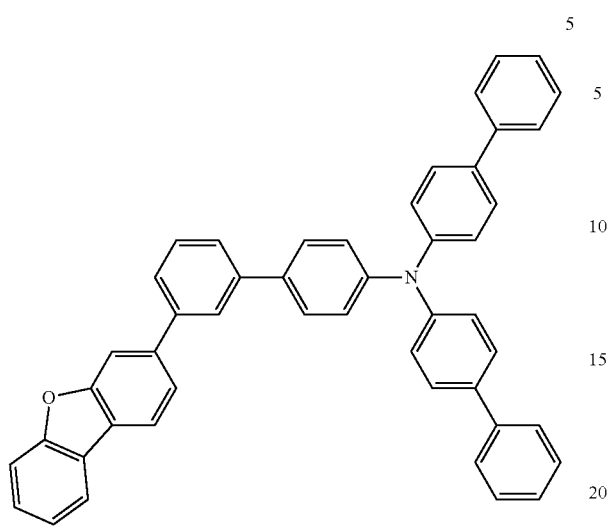
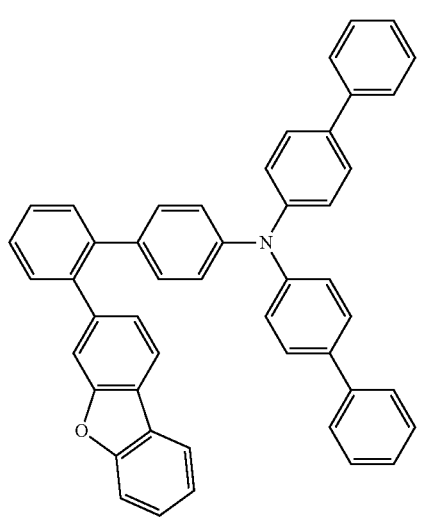
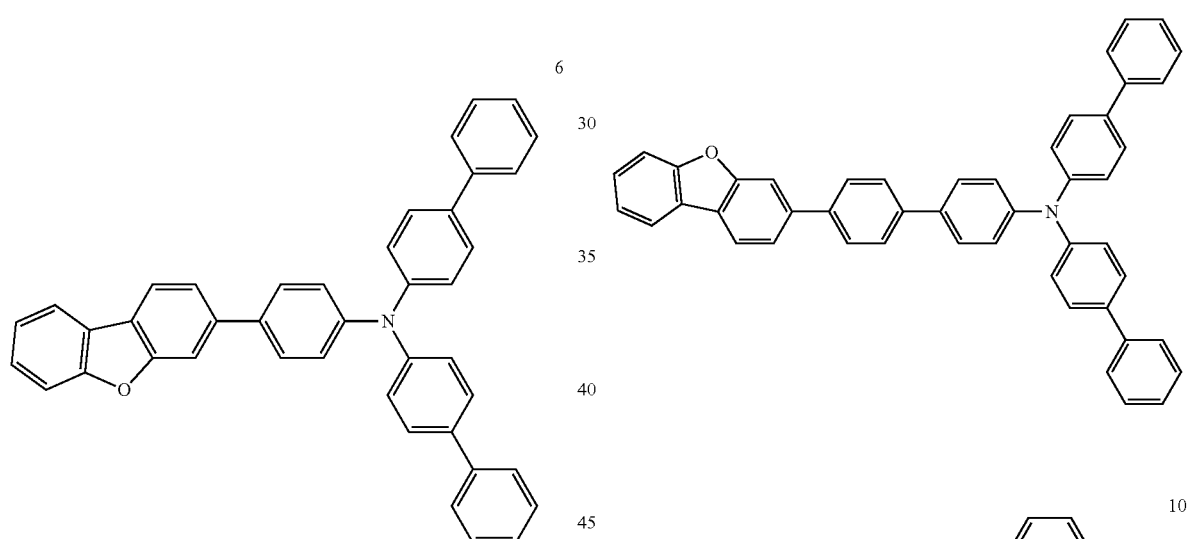
The material for an organic EL device according to an embodiment may be a material illustrated in the following structures 7 to 12.
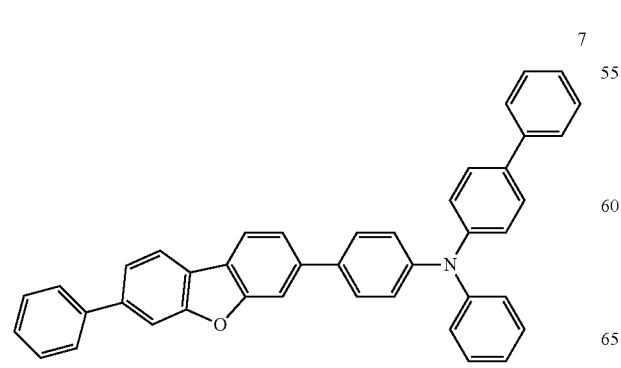
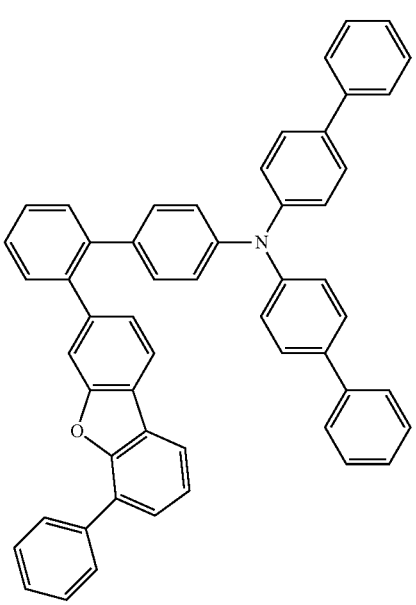

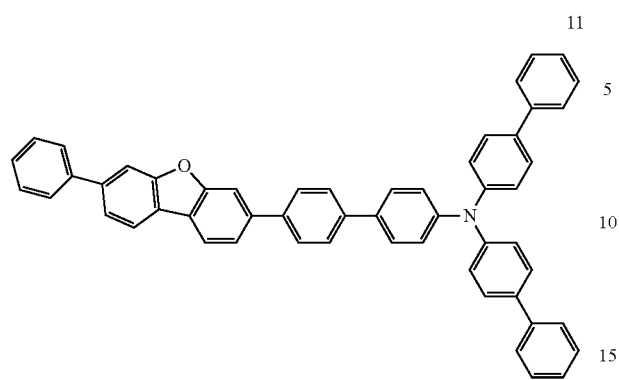
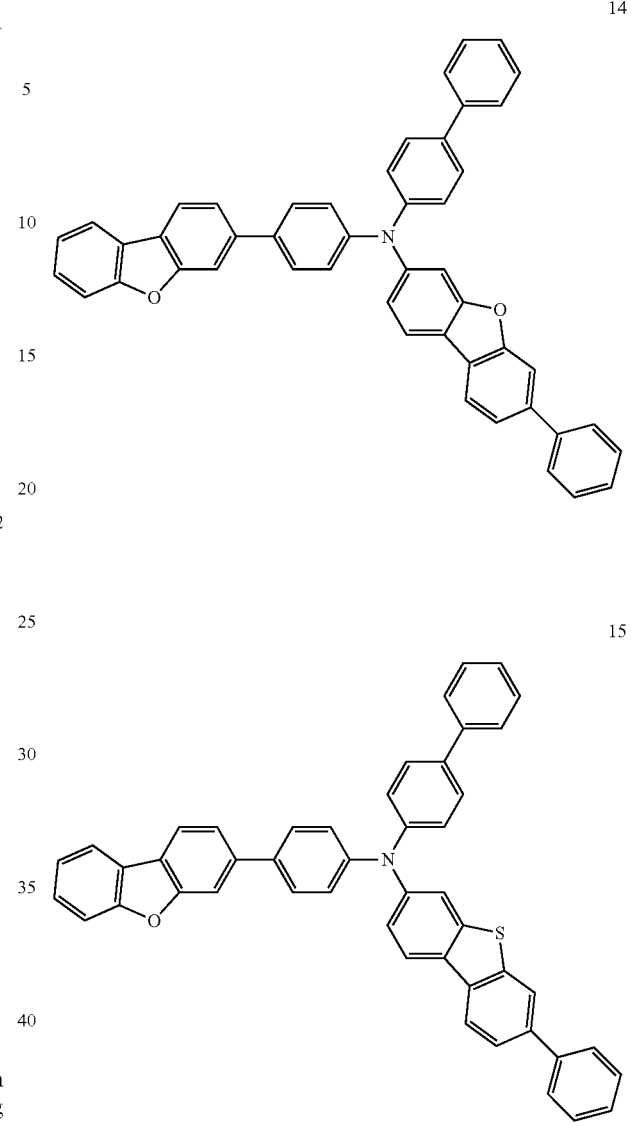
The material for an organic EL device according to an embodiment may be a material illustrated in the following structures 13 to 18.
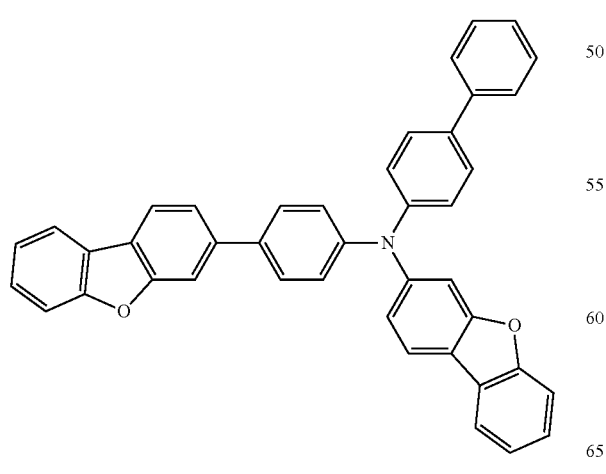
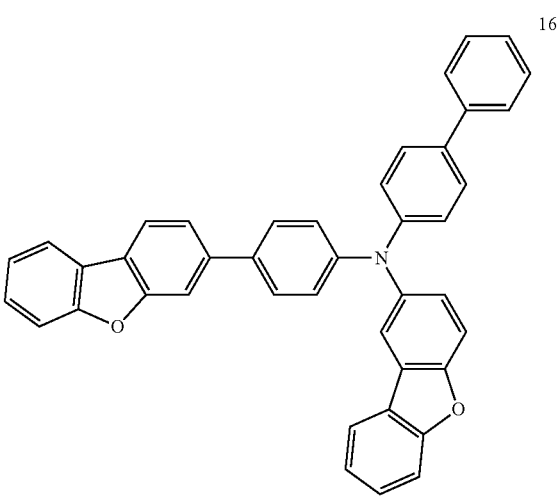

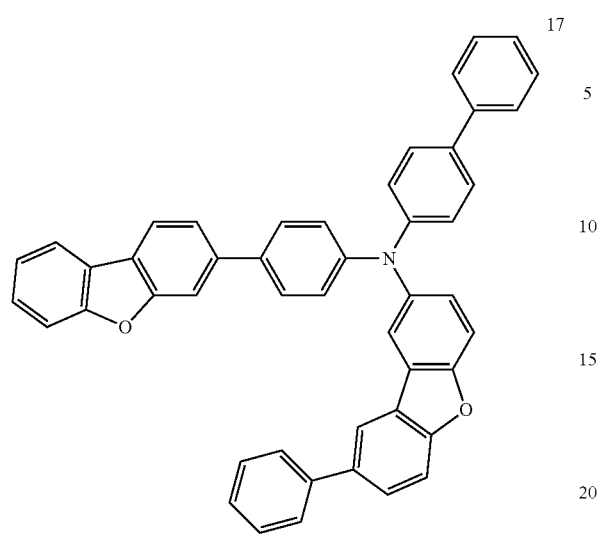
17
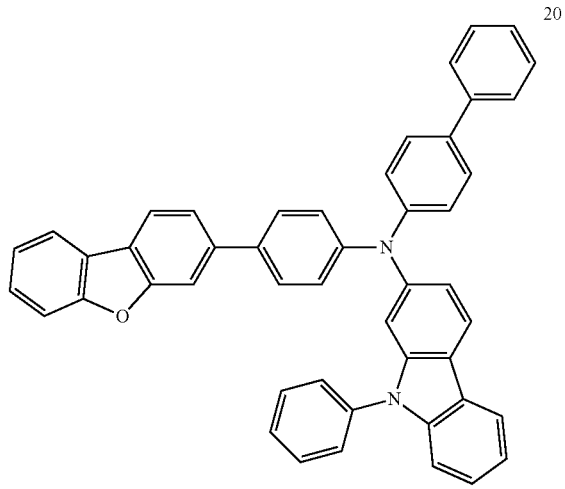
20
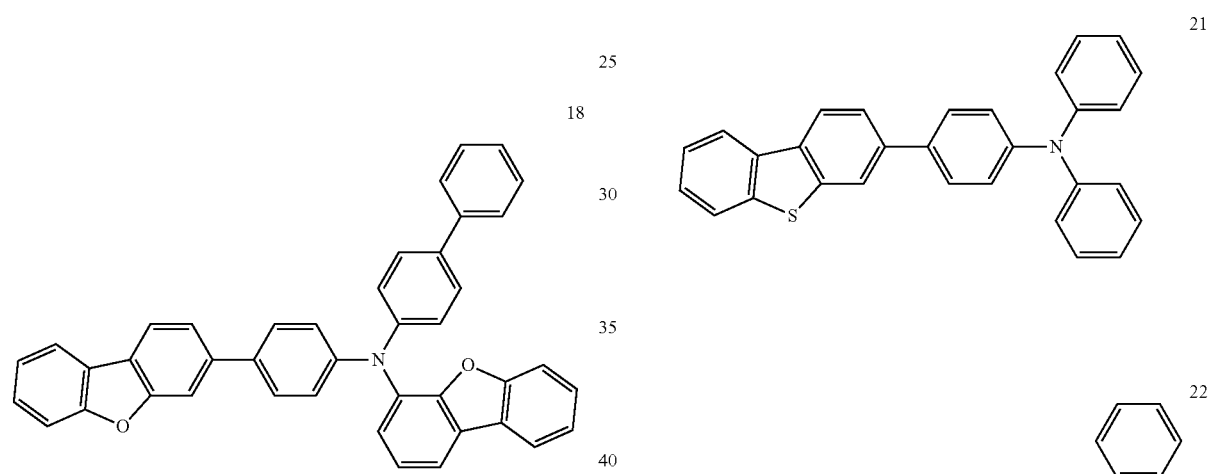
21
The material for an organic EL device according to an embodiment may be a material illustrated in the following structures 19 to 24.
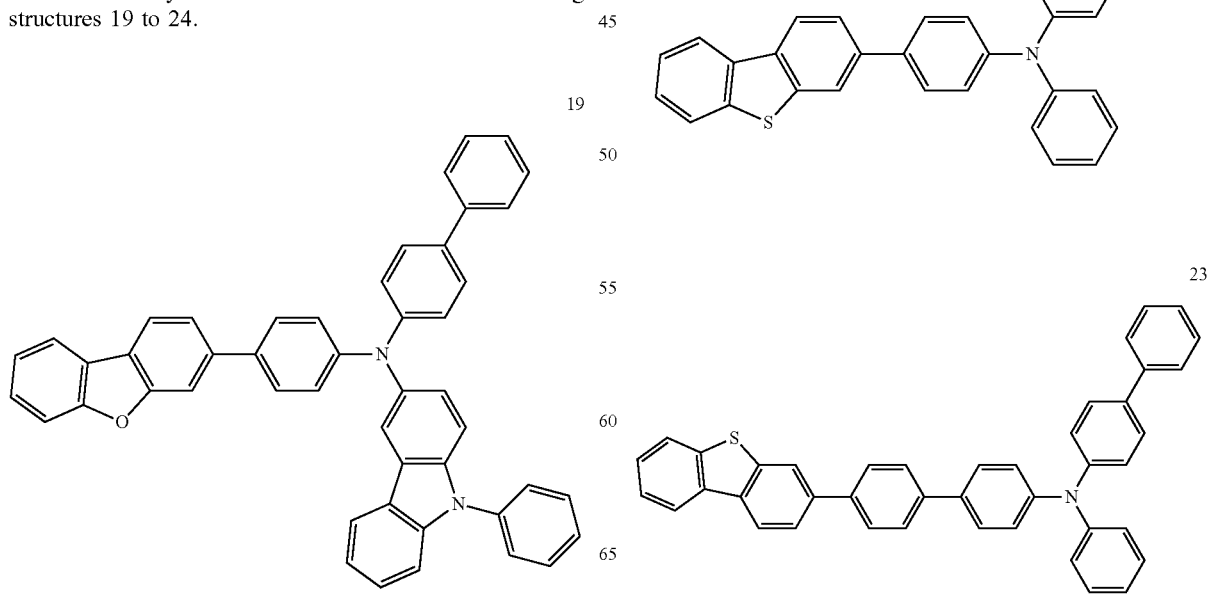

24
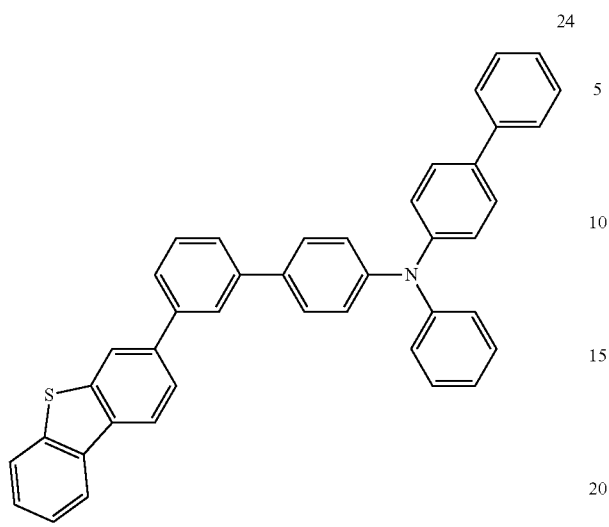
The material for an organic EL device according to an embodiment may be a material illustrated in the following structures 25 to 30.
27
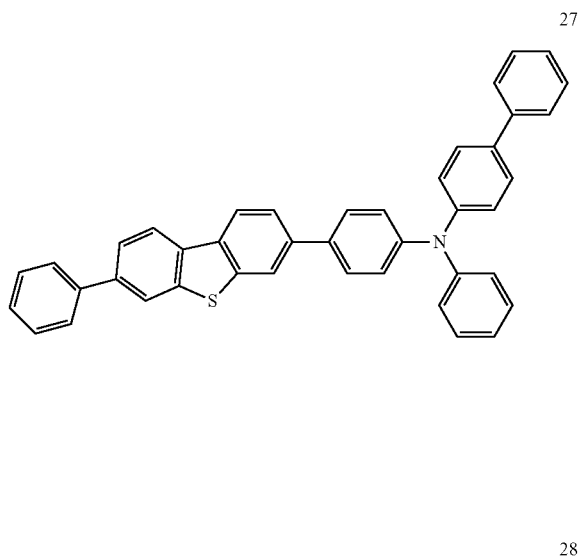
25
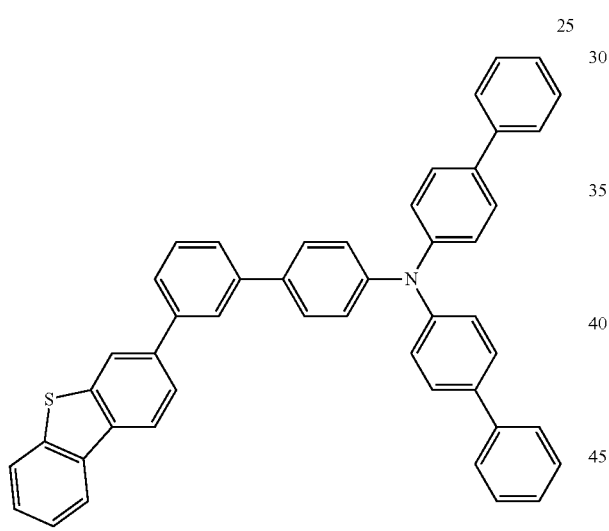
28
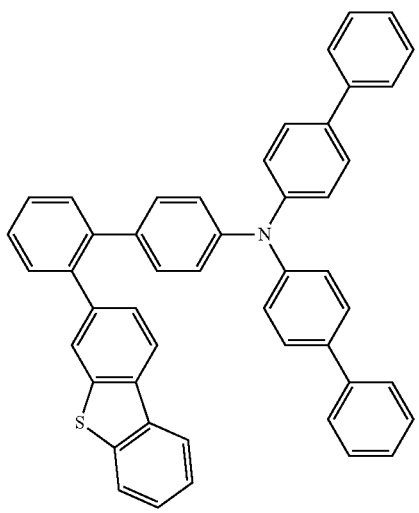
26
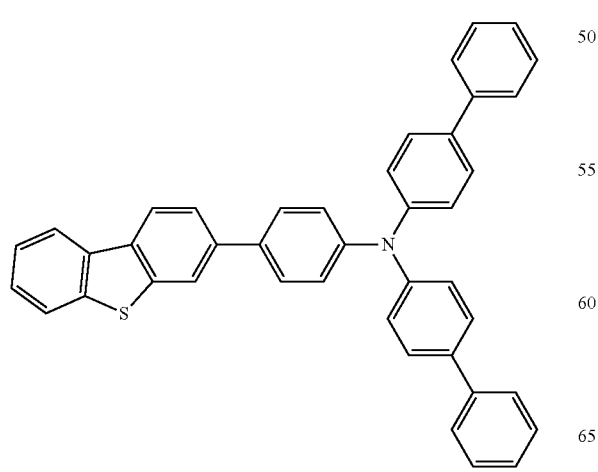
29
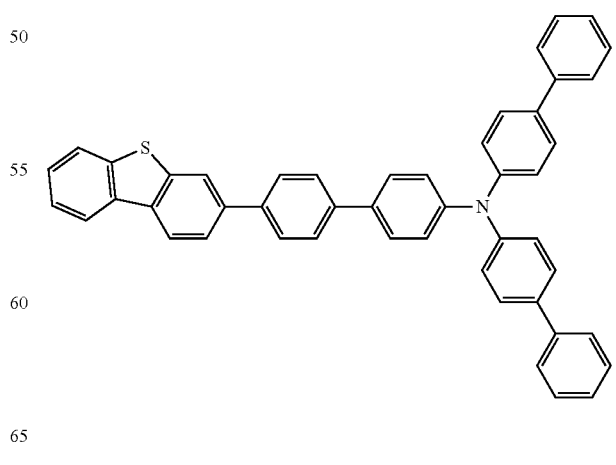

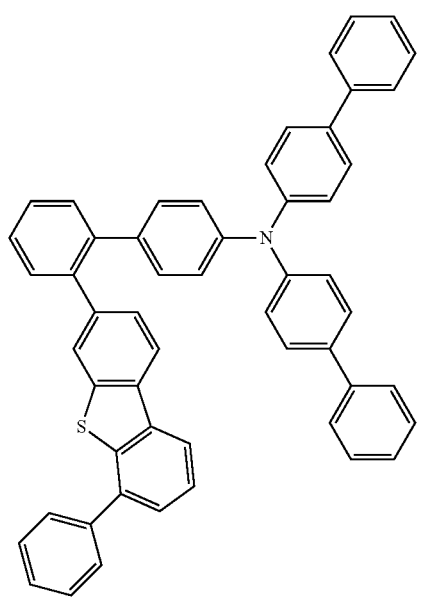
The material for an organic EL device according to an embodiment may be a material illustrated in the following structures 31 to 36.
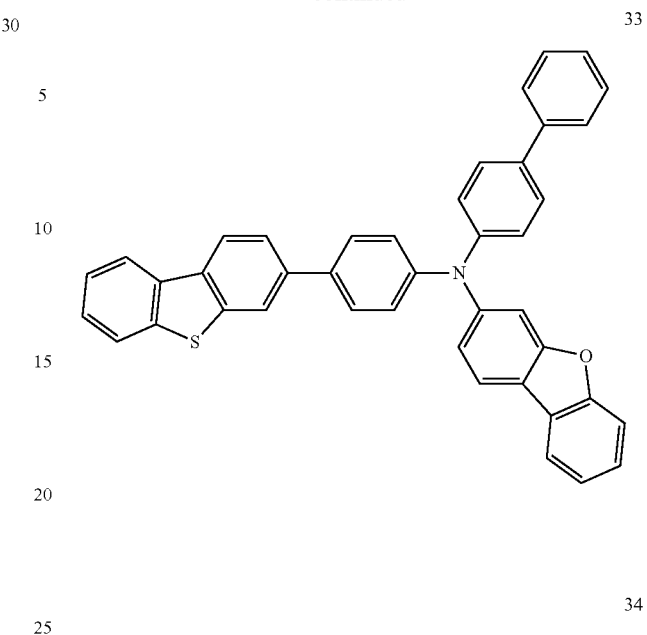
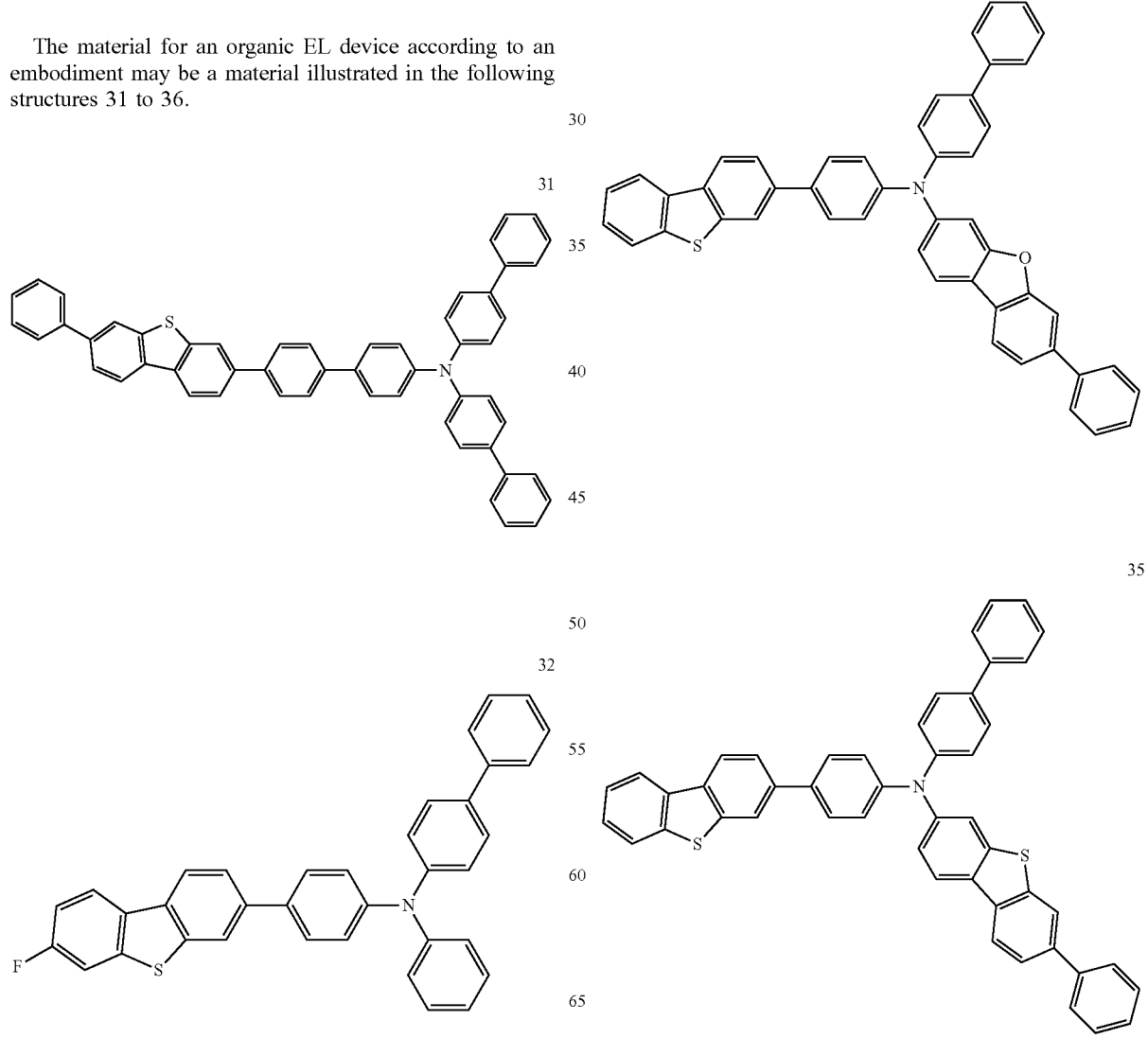

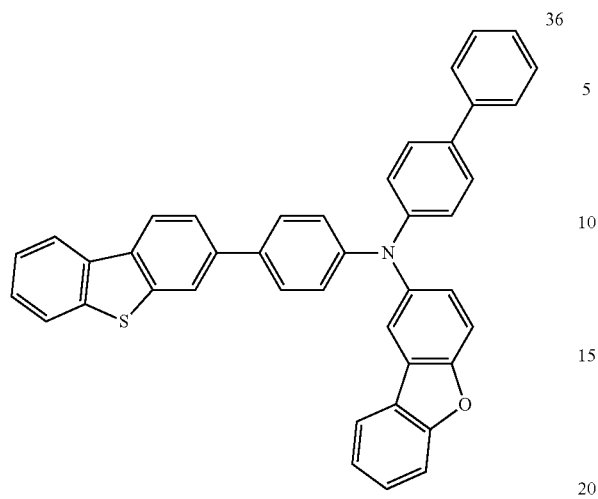
36
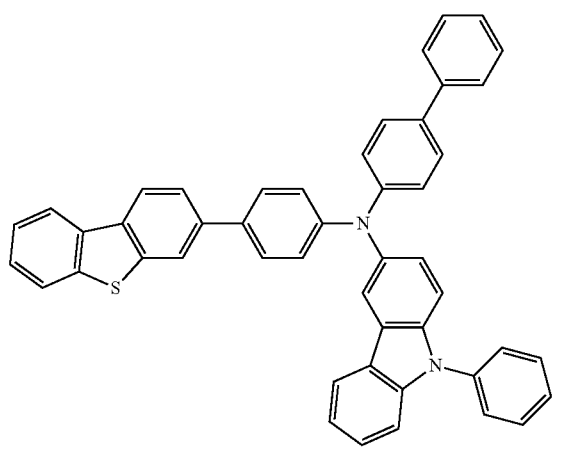
39
The material for an organic EL device according to an embodiment may be a material illustrated in the following structures 37 to 43.
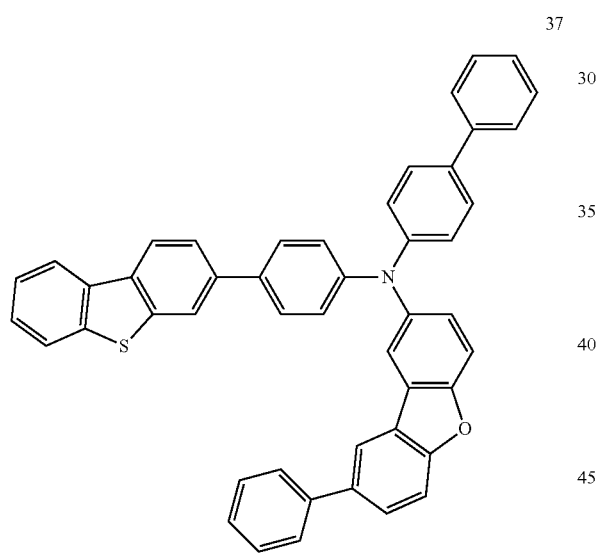
37
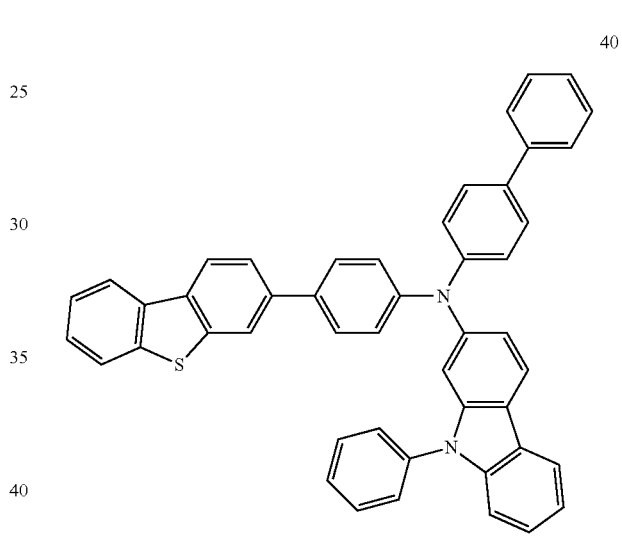
40
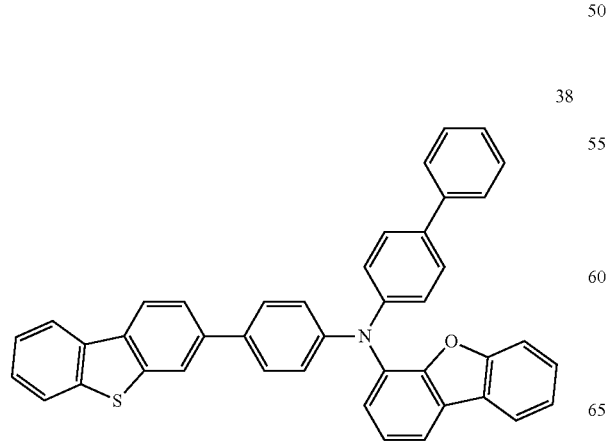
38
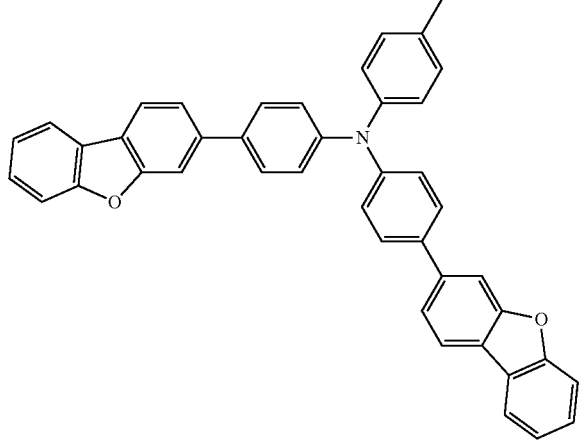
41

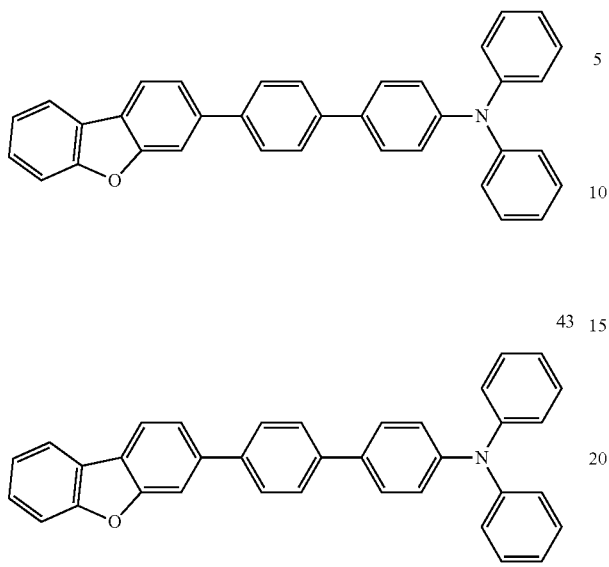

42

43

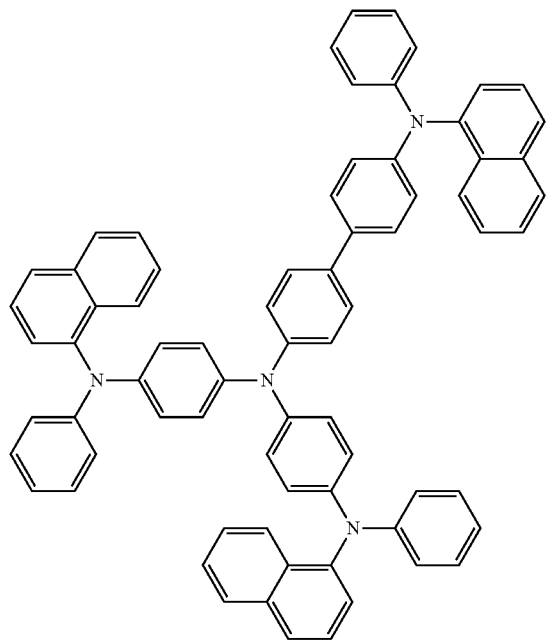

HI1

HI2

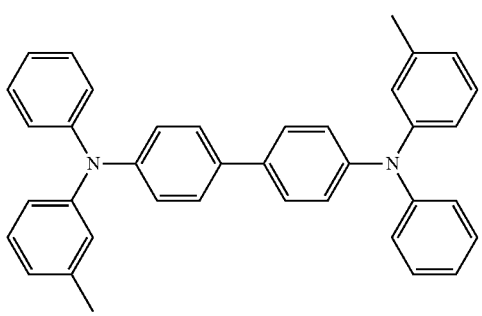

HI3

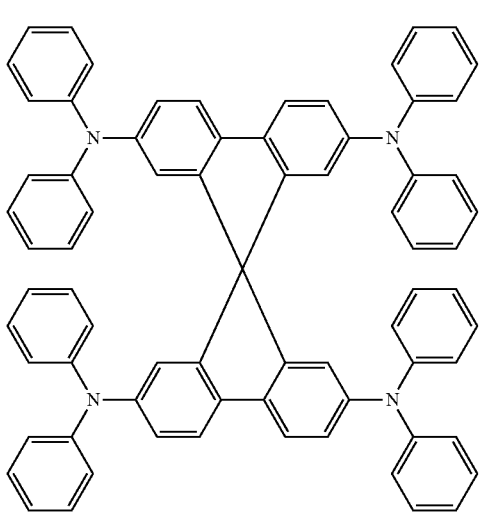

The material for an organic EL device according to embodiments may be appropriately used in an emission layer of an organic device. In addition, the material for an organic EL device according to the embodiments may be used in a layer of stacked layers disposed between the emission layer and an anode. The hole transporting properties of the organic EL device may be improved, and the long life and the high efficiency thereof may be realized.

(Organic EL Device)

An organic EL device using the material for an organic EL device according to embodiments will be explained. FIG. 1 is a schematic diagram illustrating an organic EL device 100 according to an embodiment. The organic EL device 100 may include, for example, a substrate 102, an anode 104, a hole injection layer 106, a hole transport layer 108, an emission layer 110, an electron transport layer 112, an electron injection layer 114 and a cathode 116. Suitable materials for each of these may be used. As an example, the material that was used in each layer in the Examples and Comparative Examples, below, is provided in FIG. 1. In an embodiment, the material for an organic EL device according to embodiments may be used in an emission layer of an organic EL device. In another embodiment, the material for an organic EL device may be used in a layer of stacked layers disposed between the emission layer 110 and the anode 104.

For example, an embodiment using the material for an organic EL device in the hole transport layer 108 will be explained. The substrate 102 may be a transparent glass substrate, a semiconductor substrate formed by using silicon, etc., or a flexible substrate of a resin, etc. The anode 104 may be disposed on the substrate 102. The anode 102 may be formed by using indium tin oxide (ITO), indium zinc oxide (IZO), etc.

The hole injection layer 106 My vw disposed on the anode 104. The hole injection layer 106 may include, for example, a compound of the following Compounds HI1 to HI3.

The hole transport layer 108 may be disposed on the hole injection layer 106. The hole transport layer 108 may be formed using the material for an organic EL device described above.

The emission layer 110 may be disposed on the hole transport layer 108. The emission layer 110 may include a host material represented by the following Compounds HO1 to HO4, and may be formed by doping an emission material.

HO1
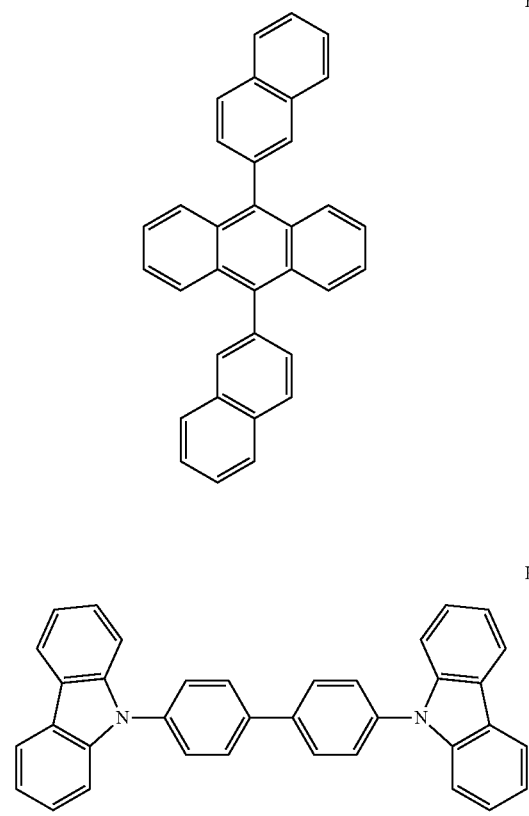
HO2
HO3
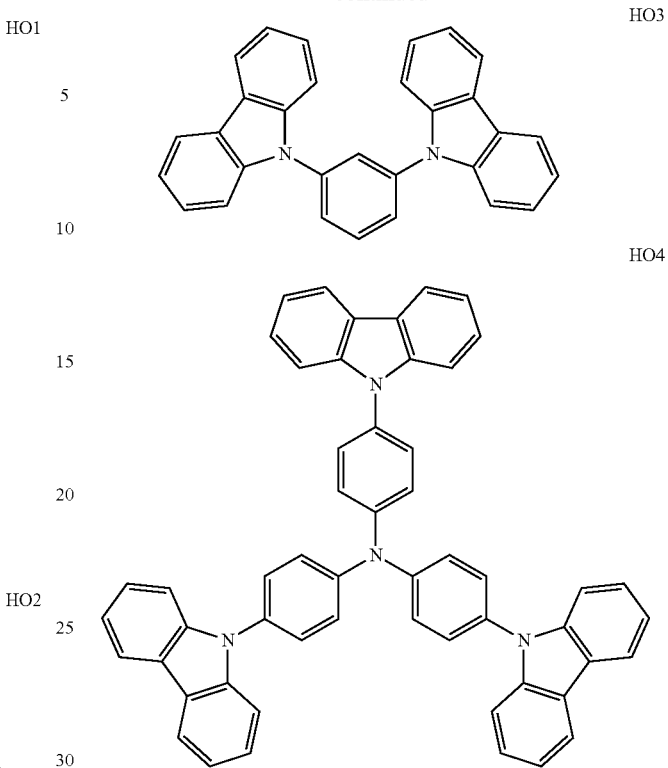
HO4
As the emission material doped in the emission layer 110, for example, a compound of the following Compounds DP1 to DP5 may be used. In addition, the emission material may be doped at an amount ratio of 0.1 to 50% with respect to a host material.
DP1
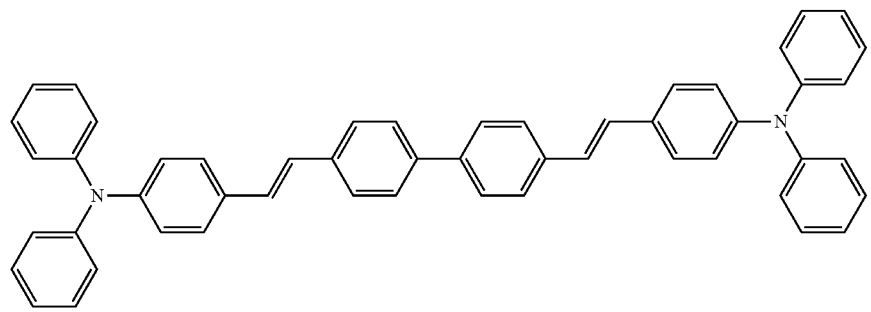
DP2
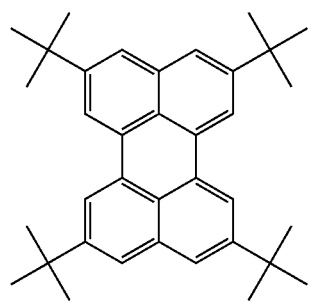
DP3
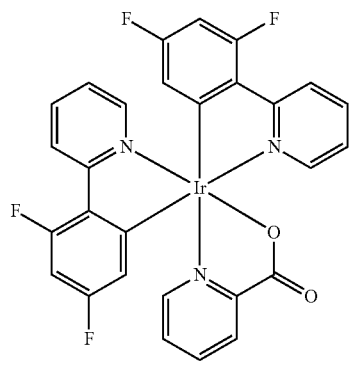

DP4

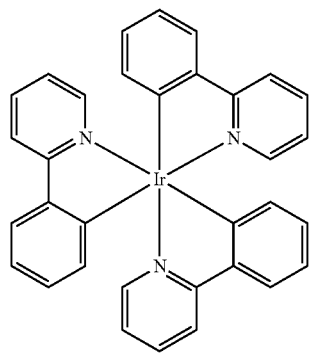

DP5

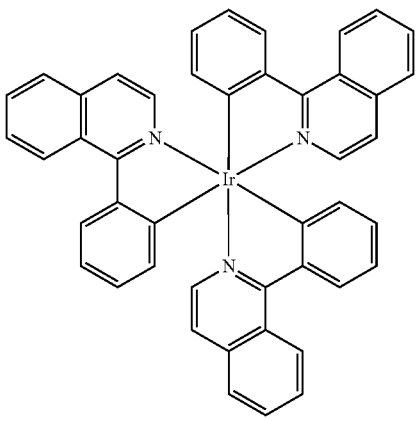

The electron transport layer 112 may be disposed on the emission layer 110. The electron transport layer 112 may include, for example, a compound of the following Compounds ET1 to ET4.

ET1

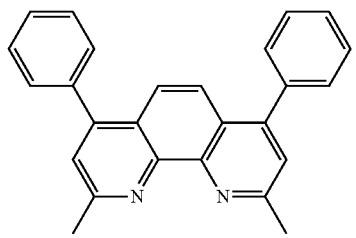

ET2

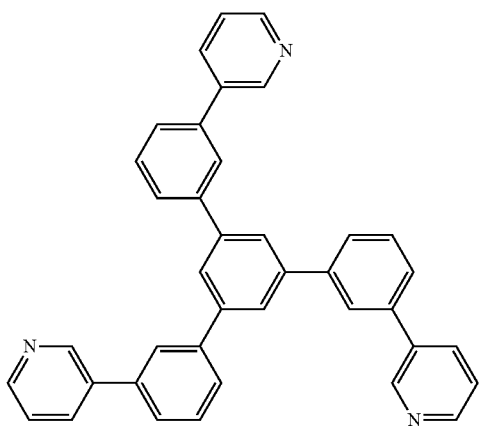

ET3

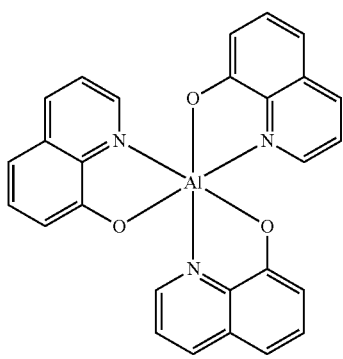

ET4

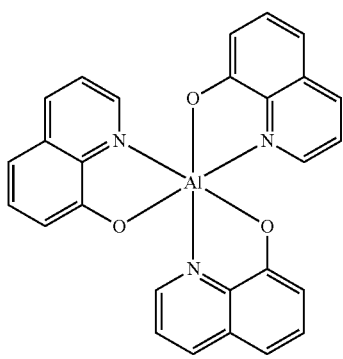

The electron injection layer 114 may be disposed on the electron transport layer 112. The electron injection layer 114 may be formed by using, for example a material including lithium fluoride (LiF). The cathode 116 may be disposed on the electron injection layer 114. The cathode may be formed by using a metal such as Al or a transparent material such as ITO, IZO, etc. The thin layers may be formed by selecting an appropriate layer forming method such as vacuum deposition, sputtering, diverse coatings, etc. according to the materials used.

In the organic EL device 100 according to an embodiment, a hole transport layer 108 having high efficiency and long life may be formed by using the material for an organic EL device. As an example, the material for an organic EL device may be applied in an organic EL apparatus of an active matrix type using thin film transistors (TFT).

The organic EL device 100 according to an embodiment includes the material for an organic EL device in an emission layer or a layer of stacked layers disposed between the emission layer and an anode. Accordingly, high efficiency and long life of the organic EL device may be realized.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES (Preparation Method)

The above-described materials for an organic EL device may be synthesized, for example, by the following methods.

(Synthesis of Compound 6)

4.2 g of 4-bis(biphenylyl)aminophenyl boronic acid pinacol ester, 2 g of 3-bromodibenzofuran, 0.1 g of tetrakis(triphenylphosphine)palladium(0), 3.3 g of potassium carbonate, 180 ml of tetrahydrofuran, and 20 ml of water were added in a 500 ml, three-necked flask under an argon atmosphere, followed by heating while refluxing at 80° C. for 12 hours. After cooling in the air, water was added to the flask, and an organic layer was separated. The solvent was distilled, and the solid thus obtained was separated by flash column chromatography to produce 3.6 g of Compound 6 as white solid (yield 80%).

(Identification of Compound 6)

The molecular weight of Compound 6 measured by FAB-MS was 563.7.

Organic EL devices according to Examples 1 to 3 were manufactured using the above Compounds 2, 6, and 26 as hole transport materials by the above-described method, and an organic EL device according to Example 4 was manufactured using Compound 13 as a hole transport material. Compounds 2, 13, and 26 were synthesized in a similar reaction scheme as described above with respect to claim 6 by selecting the appropriate starting materials. In addition, organic EL devices according to Comparative Examples 1 to 5 were manufactured using the following Compounds 51 to 55 as hole transport materials for comparison. Compounds 51 to 55 are Comparative Compounds.

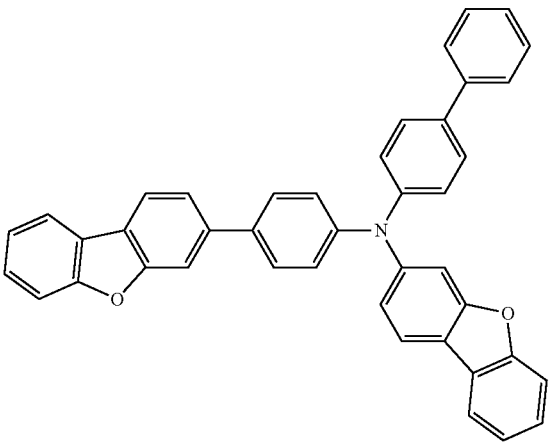

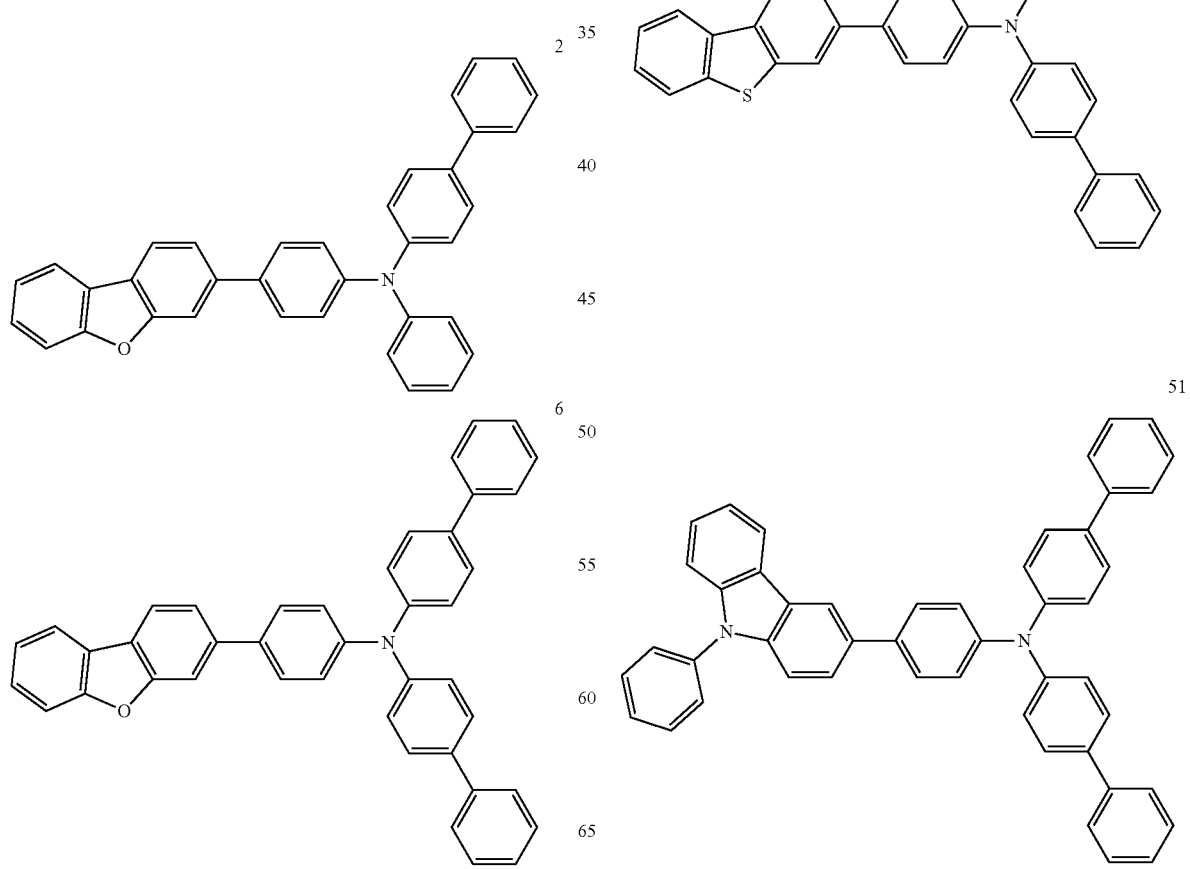

-continued

52
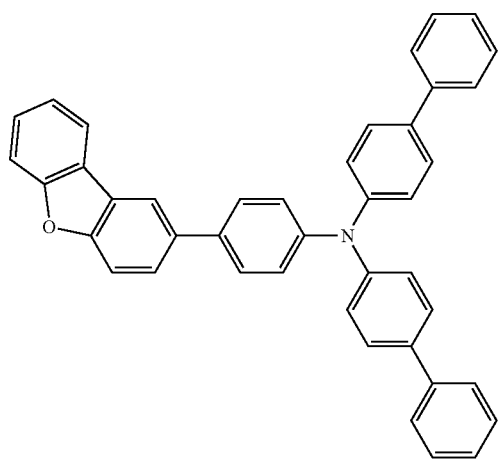

53
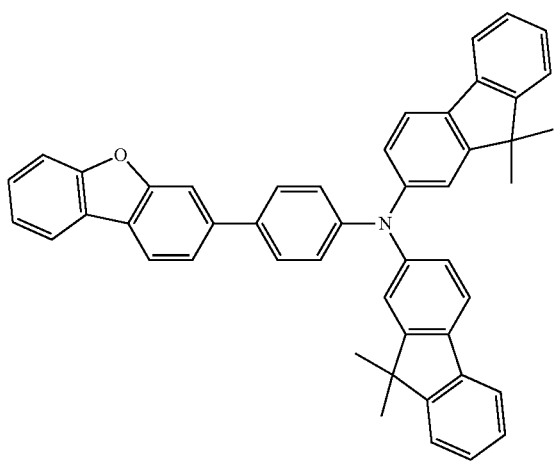

54
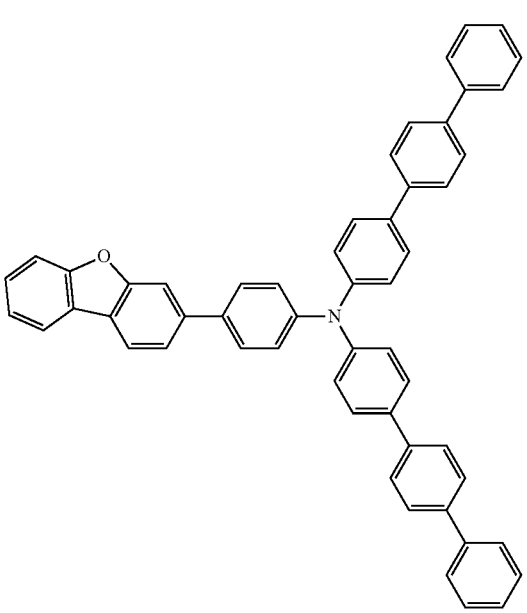

-continued

55
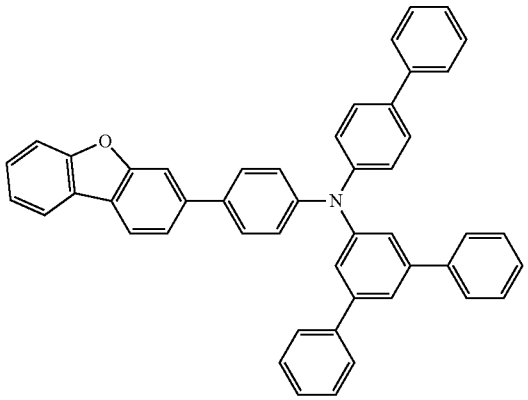

The organic EL devices were formed as stacked layers as illustrated in FIG. 1. The substrate 102 was formed using a transparent glass substrate, the anode 104 was formed using ITO to a thickness of about 150 nm, the hole injection layer 106 was formed using TNATA (HI1, above) to a thickness of about 60 nm, the hole transport layer 108 was formed using the compounds of the examples or the comparative examples to a thickness of about 30 nm, the emission layer 110 was formed using ADN (9,10-di(2-naphthyl)anthracene) (HO1, above) doped with 3% TBP(2,5,8,11-tetra-t-butylperylene) (DP2, above) to a thickness of about 25 nm, the electron transport layer 112 was formed using Alq$_3$ (ET3, above) to a thickness of about 25 nm, the electron injection layer 114 was formed using LiF to a thickness of about 1 nm, and the cathode 116 was formed using Al to a thickness of about 100 nm.

With respect to the organic EL devices thus manufactured, the voltage, the emission efficiency and the life were evaluated. The evaluation was conducted at the current density of 10 mA/cm$^2$.

TABLE 1

| Device manufacturing Example | Hole transport layer | Voltage (V) | Emission efficiency (cd/A) | Life LT50 (h) |
|---|---|---|---|---|
| Example 1 | Exemplary Compound 2 | 7.5 | 8.9 | 3,800 |
| Example 2 | Exemplary Compound 6 | 8.1 | 8.7 | 4,700 |
| Example 3 | Exemplary Compound 26 | 6.9 | 9.2 | 2,200 |
| Example 4 | Exemplary Compound 13 | 6.7 | 9.0 | 2,000 |
| Comparative Example 1 | Comparative Compound 51 | 7.5 | 5.2 | 1,800 |
| Comparative Example 2 | Comparative Compound 52 | 8.1 | 6.3 | 900 |
| Comparative Example 3 | Comparative Compound 53 | 7.6 | 8.8 | 1,800 |
| Comparative Example 4 | Comparative Compound 54 | 7.5 | 8.3 | 2,200 |
| Comparative Example 5 | Comparative Compound 55 | 7.6 | 8.8 | 1,600 |

Referring to the results in Table 1, the organic EL devices according to Examples 1 to 4 have higher efficiency and longer life when compared to those according to the comparative examples. When comparing Example 2 with Comparative Example 2, the organic EL device using an amine compound combined with a dibenzofuranyl group at position 3 via a phenylene group in the hole transport layer 108 according to Example 2 has longer life and higher efficiency when compared to the organic EL device using an amine compound making a combination at position 2 in the hole transport layer 108 according to Comparative Example 2, thereby verifying the effects depending on combining position. Without being bound to theory, it is believed that in the organic EL device using the amine compound combined at position 3 in the hole transport layer 108 according to Example 2, the inflow of electrons from the emission layer 110 may be restrained. However, in the organic EL device using the amine compound combined at position 2 in the hole transport layer 108 according to Comparative Example 2, the blocking performance of electrons may be decreased, and electrons from the emission layer 110 may intrude into the hole transport layer 108. Thus, a decrease of recombination and deterioration of the hole transport layer 108 may be generated. In addition, when comparing Example 2 and Example 3, the realization of the long life of the organic EL device may be clearly favorable when introducing the dibenzofuranyl group instead of the dibenzothiophenyl group. In addition, in the case that Compound 13 in which heterocyclic structures are introduced as $Ar_1$ or $Ar_2$, was used in the hole transport layer 108, the effects of a low voltage and high efficiency may be positively obtained as in Example 4.

In addition, when $Ar_1$ and $Ar_2$ are aryl groups and when Compound 6 in which $Ar_1$ and $Ar_2$ are the biphenylyl groups as in Example 2, a device having the longest life may be manufactured. In Comparative Examples 3 to 5, in which substituents having greater molecular weights than the biphenylyl group as $Ar_1$ and $Ar_2$ are included, the same or better results were obtained for the voltage, the emission efficiency, etc., however the lowering of the life was recognized. Without being bound to theory, adverse effects on the life of the device are considered to have resulted through the deterioration of sublimation properties due to the increase of the molecular weight and the increase of a π-π interaction, and through the generation of impurities by the partial decomposition of 3-dibenzofuranyl group due to the increase of a layer manufacturing temperature.

By way of summation and review, in the application of an organic EL device in a display apparatus, high efficiency and long life of the organic EL device are desirable. Particularly, the emission efficiency and the life of the organic EL device in a blue emission region may be insufficient when compared to those in a red emission region or a green emission region. To realize the high efficiency and the long life of the organic EL device, the normalization and the stabilization of a hole transport layer have been examined to realize the high efficiency and the long life of the organic EL device. Hole transport materials used in the hole transport layer may generally include a compound including carbazole or amine or a compound obtained by combining these, such as a compound including dibenzofuran and an amine. For example, an amine compound may include fluorene and dibenzofuran or may include a terphenyl group and dibenzofuran. However, when using a compound including a terphenyl group or a fluorene ring structure in a manufacturing process of a layer, thermal decomposition of a material due to the increase of a depositing temperature may be generated.

Other general materials include a polyamine compound containing dibenzofuran and at least two combined amine parts, an amine compound containing carbazole and dibenzofuran, a dibenzofuran derivative, an anthracene derivative containing dibenzofuran and amine as substituents, a compound in which an amino group is directly combined with dibenzofuran, dibenzofuran combined with a substituent containing amine at position 2, a structure in which 3-dibenzofurane group-phenyl group-amine are connected in order, an amine derivative containing a deuterated phenyl group, a monoamine material containing diphenyl or triphenylated phenyl group and dibenzofuran, a monoamine material containing a plurality of dibenzofurans combined at position 3, a monoamine material containing one dibenzofuran combined at a position other than position 3, as a host material in one emission layer in an organic EL device including a plurality of emission layers, and monoamine materials combined with carbazole and dibenzofuran at position 3.

However, the organic EL devices using the above-described materials may have insufficient emission efficiency and emission life. An organic EL device having higher emission efficiency and longer life is desirable.

Embodiments provide a material in which an amine compound is combined with a dibenzofuranyl group or a dibenzothiophenyl group at position 3 via a connecting group instead of a general material in which an amine compound is combined with a dibenzofuranyl group or a dibenzothiophenyl group at position 2 via a connecting group. Embodiments provide a material for an organic electroluminescence device having high efficiency and long life in a blue emission region, and an organic electroluminescence device using the same. For example, embodiments provide a material for an organic EL device having high efficiency and long life and used in an emission layer or a layer of stacking layers disposed between the emission layer and an anode, and an organic EL device using the same.

The long life and the high efficiency of an organic EL device may be realized by using the material for an organic EL device according to an embodiment, in which an amine compound is combined with a dibenzofuranyl group with high hole tolerance and electron tolerance at position 3 via a phenylene group or a biphenylene group when compared to a common and widely known material in which an amine compound makes a combination at position 2. In addition, the thermal decomposition of a layer of the organic EL device during forming thereof by a deposition method may be restrained by limiting the number of the atom for forming a ring of $Ar_1$ and $Ar_2$ and the number of the atom of a substituent at the dibenzofuranyl group.

In other embodiments, organic EL devices include the material for an organic EL device described above in an emission layer.

In the organic EL device according to an embodiment, longer life and higher efficiency may be realized by using an amine compound combined with a dibenzofuranyl group or a dibenzothiophenyl group with high hole tolerance and electron tolerance at position 3 via a phenylene group or a biphenylene group in forming an emission layer when compared to a common amine compound making a combination at position 2. In addition, the thermal decomposition of a layer of the organic EL device during forming thereof by a deposition method may be restrained by limiting the number of the atom for forming a ring of $Ar_1$ and $Ar_2$.

In still other embodiments, organic EL devices include the material for an organic EL device described above in a layer of stacked layers disposed between an emission layer and an anode.

In the organic EL device according to an embodiment, long life and high efficiency may be realized by using an amine compound combined with a dibenzofuranyl group or a dibenzothiophenyl group with high hole tolerance and electron tolerance at position 3 via a phenylene group or a biphenylene group in forming a layer of stacking layers disposed between an emission layer and an anode. In addition, the thermal decomposition of a layer of stacked layers disposed between an emission layer and an anode of the organic EL device during forming thereof by a deposition method may be restrained by limiting the number of the atom for forming a ring of $Ar_1$ and $Ar_2$.

Embodiments provide a material for an organic EL device having high efficiency and long life and an organic EL device using the same. A material for an organic EL device having high efficiency and long life may be used in an emission layer or a layer of stacking layers disposed between the emission layer and an anode, and an organic EL device using the same are provided.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A material for an organic electroluminescence (EL) device represented by the following Formula 1:

[Formula 1]

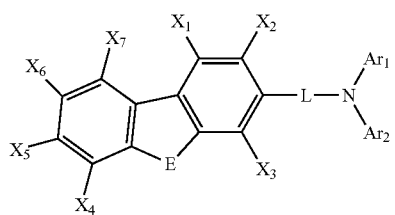

(1)

where X1 to X7 are each a hydrogen atom,
$Ar_1$ and $Ar_2$ are independently a substituted or unsubstituted aryl group having 6 to 12 ring carbon atoms, or a substituted or unsubstituted heteroaryl group having 5 to 13 ring carbon atoms,
L is a divalent connecting group represented by the following Formula 2,
n is 1 or 2, and
E represents an oxygen atom or a sulfur atom,

[Formula 2]

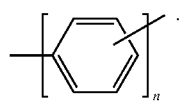

(2)

2. The material for an organic EL device as claimed in claim 1, wherein $Ar_1$ is an aryl group having 6 to 12 ring carbon atoms.

3. The material for an organic EL device as claimed in claim 1, wherein E is an oxygen atom.

4. The material for an organic EL device as claimed in claim 1, wherein $Ar_2$ is one of the following Groups (3) to (5):

(3)

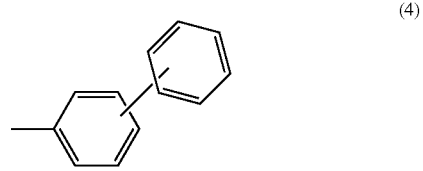

(4)

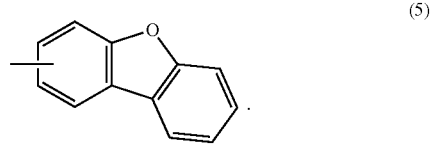

(5)

5. The material for an organic EL device as claimed in claim 1, wherein the material is one of Compounds (6) to (11):

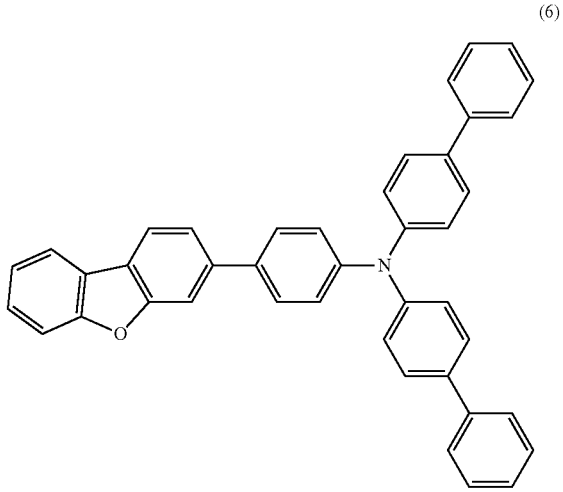

(6)

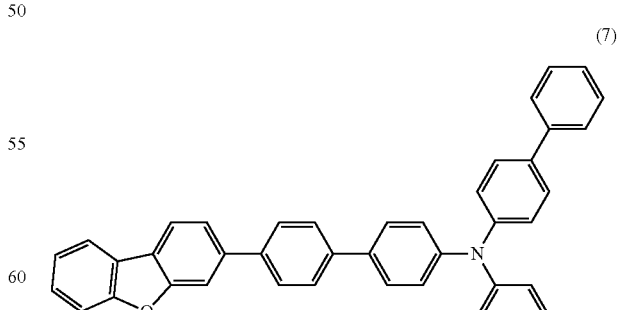

(7)

-continued (8)
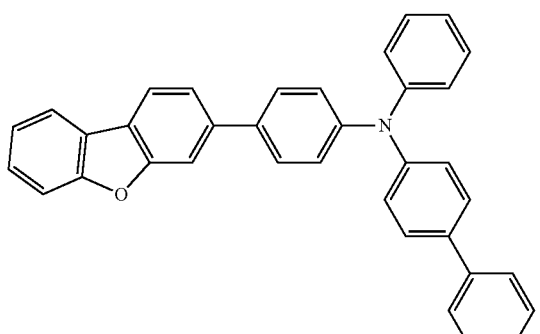

(9)
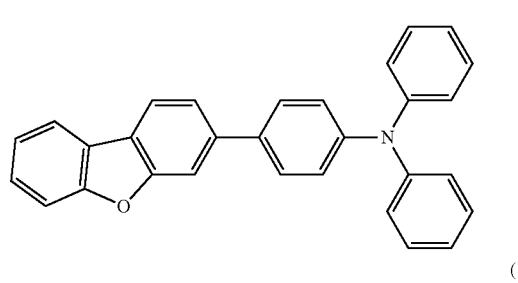

(10)
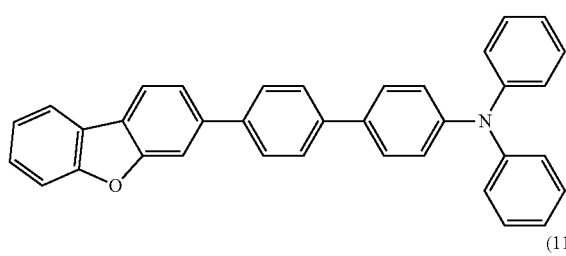

(11)
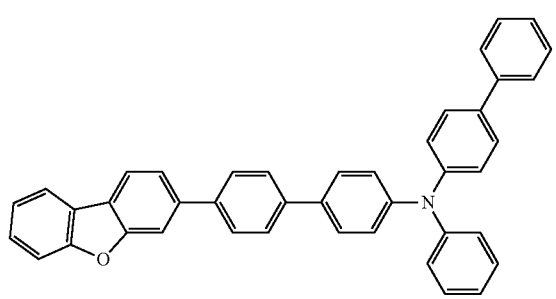

6. An organic electroluminescence (EL) device, comprising a material for an organic EL device represented by the following Formula 6:

[Formula 6]

(6)
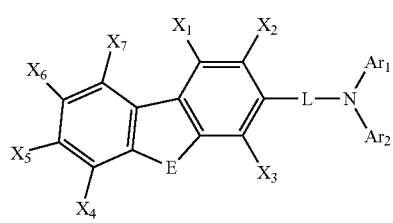

where $X_1$ to $X_7$ are each a hydrogen atom,
Ar$_1$ and Ar$_2$ are independently a substituted or unsubstituted aryl group having 6 to 12 ring carbon atoms, or a substituted or unsubstituted heteroaryl group having 5 to 13 ring carbon atoms, L is a divalent connecting group represented by the following Formula 2,
n is 1 or 2, and
E represents an oxygen atom or a sulfur atom,

[Formula 2]

(2)
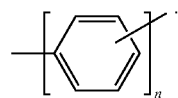

7. The organic EL device as claimed in claim 6, wherein the material for an organic EL device is included in an emission layer.

8. The organic EL device as claimed in claim 6, wherein the material for an organic EL device is included in a layer of stacked layers located between an emission layer and an anode.

9. The organic EL device as claimed in claim 6, wherein Ar$_1$ is an aryl group having 6 to 12 ring carbon atoms.

10. The organic EL device as claimed in claim 6, wherein E is an oxygen atom.

11. The organic EL device as claimed in claim 6, wherein Ar$_2$ is one of the following Groups (8) to (10):

(8)
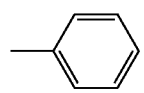

(9)
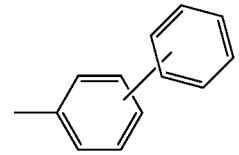

(10)
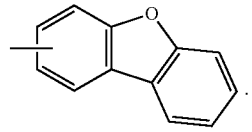

12. The organic EL device as claimed in claim 6, wherein the material for an organic EL device includes one of the following Compounds 1 to 6:

1
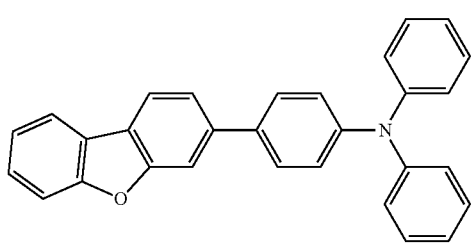

2
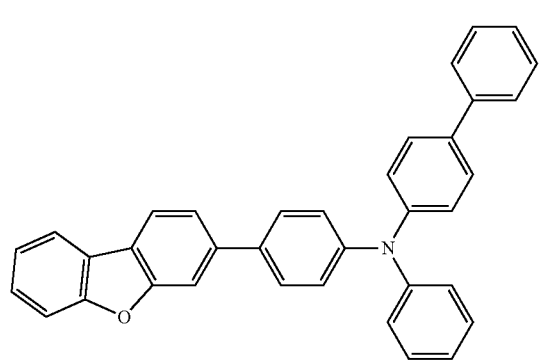
3
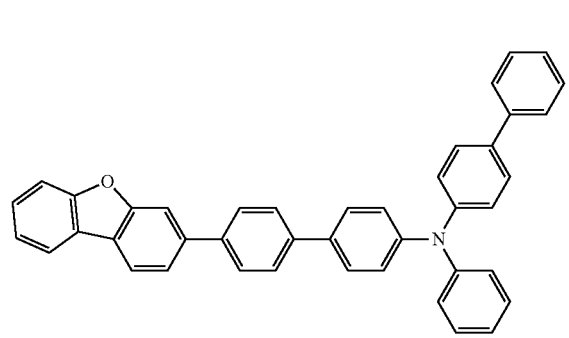
4
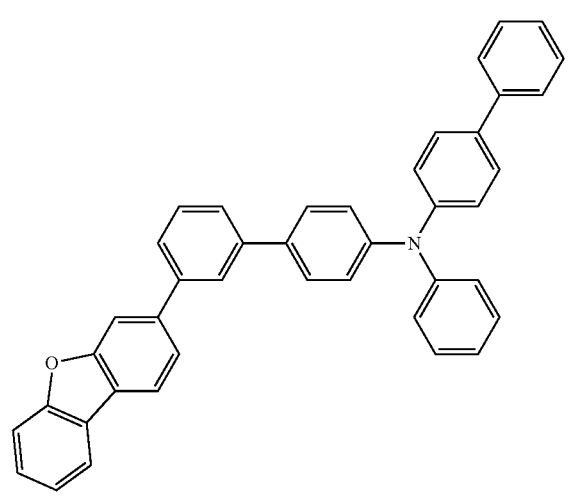
5
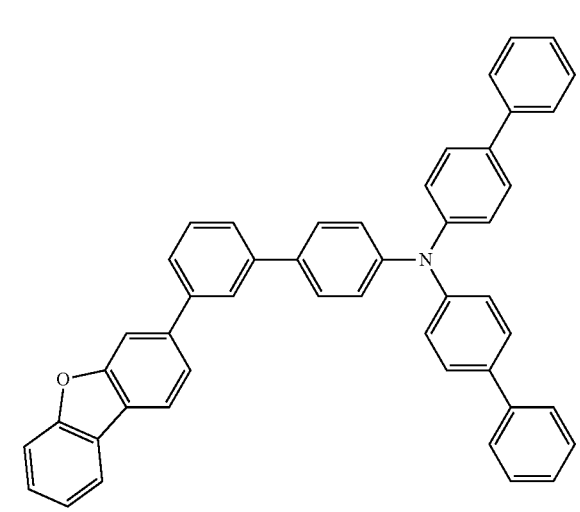
6
13. The organic EL device as claimed in claim 6, wherein the material for an organic EL device includes at least one of Compounds 8, 9, and 13 to 18:
8
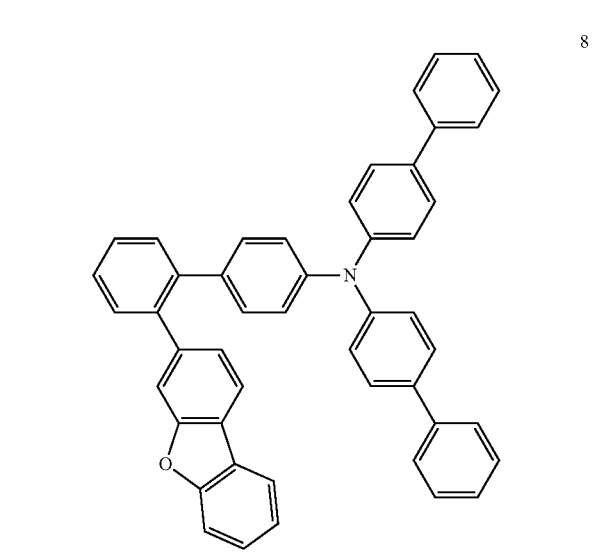

-continued
9
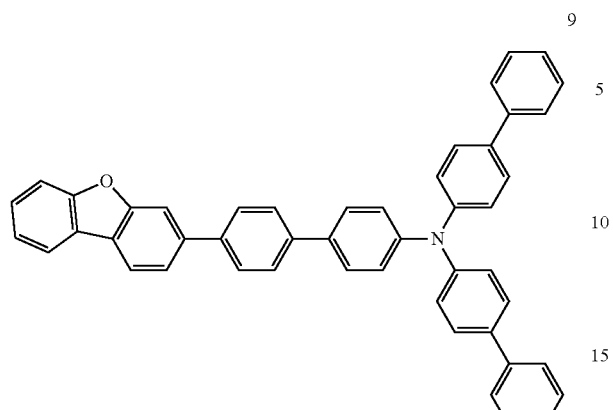
13
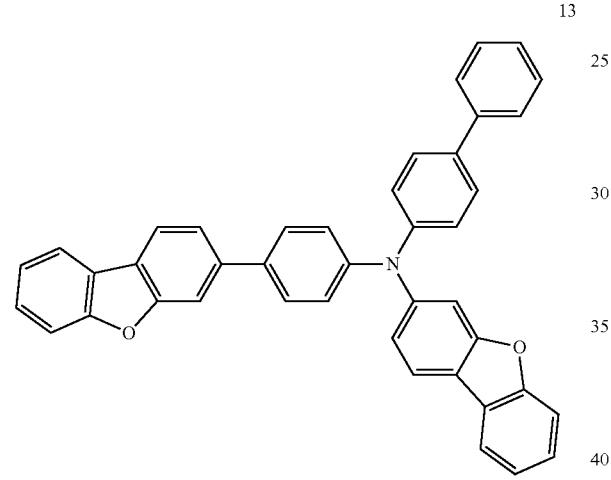
14
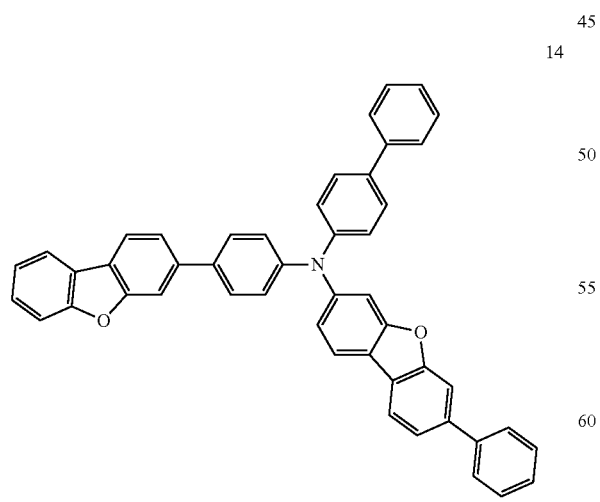
-continued
15
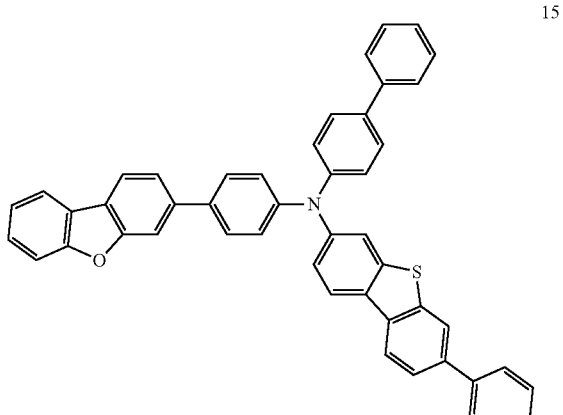
16
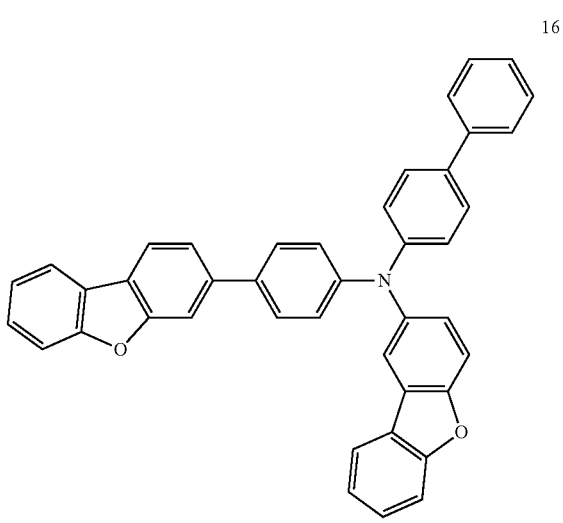
17
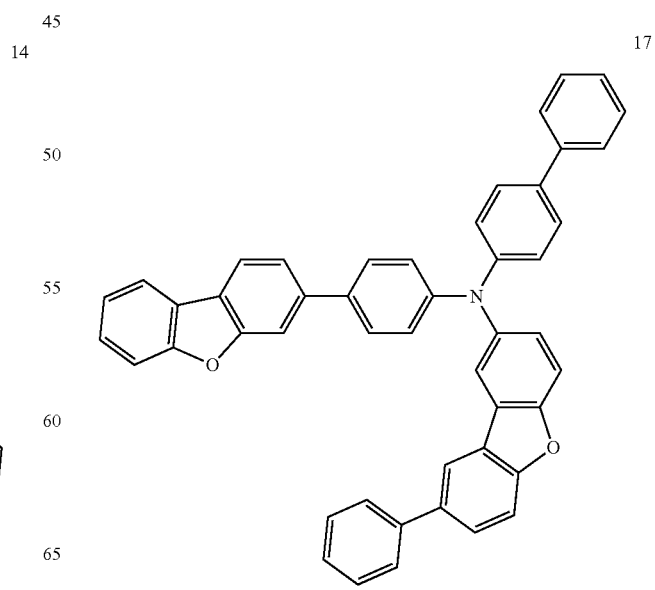

18
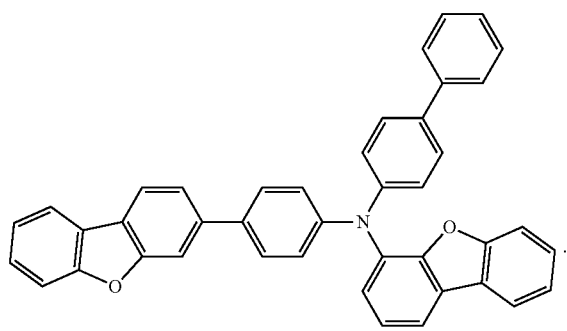
14. The organic EL device as claimed in claim 6, wherein the material for an organic EL device includes at least one of Compounds 19 to 26 and 28 to 29:
19
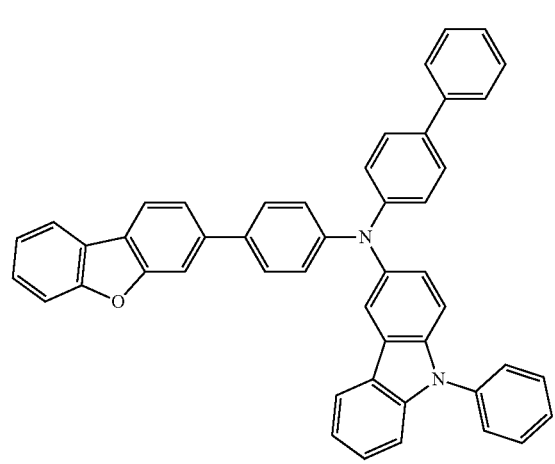
20
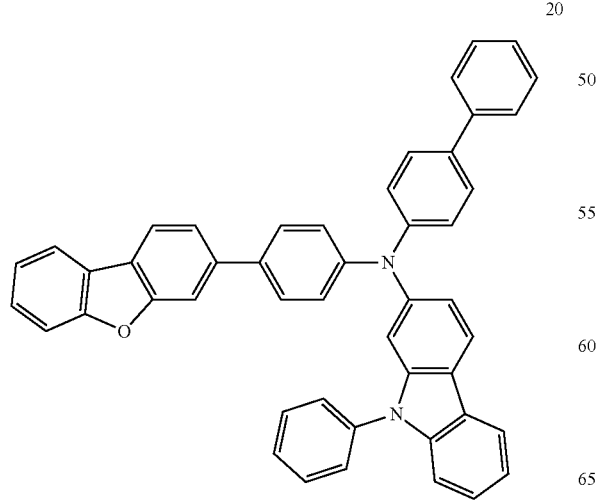
21
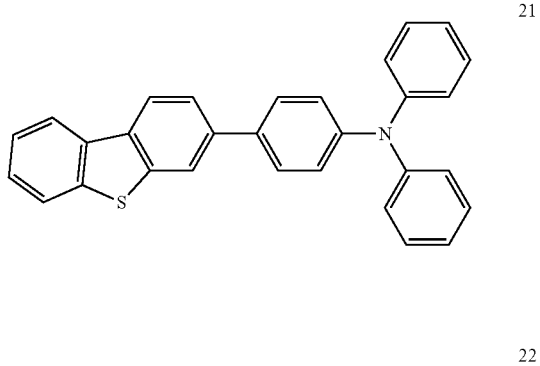
22
23
24
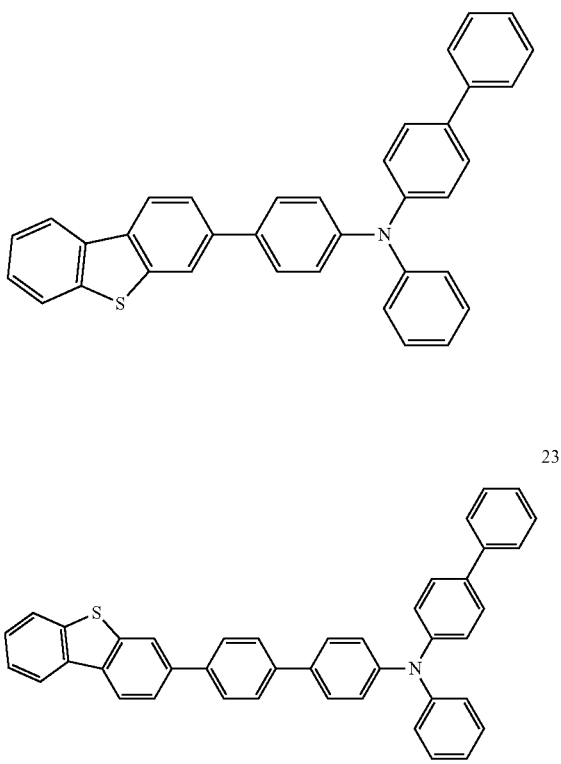
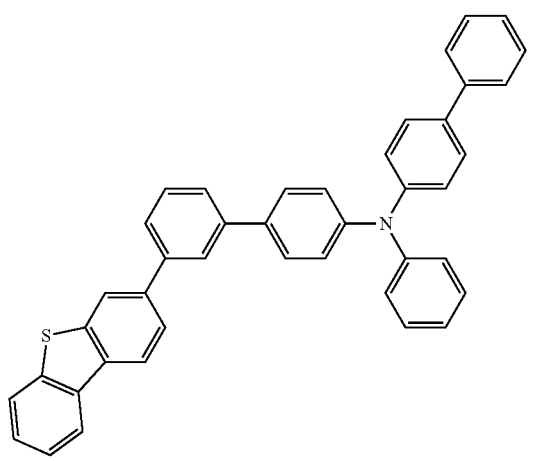

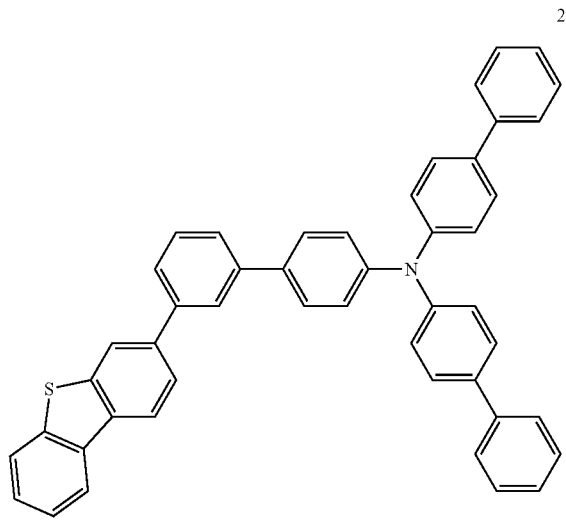
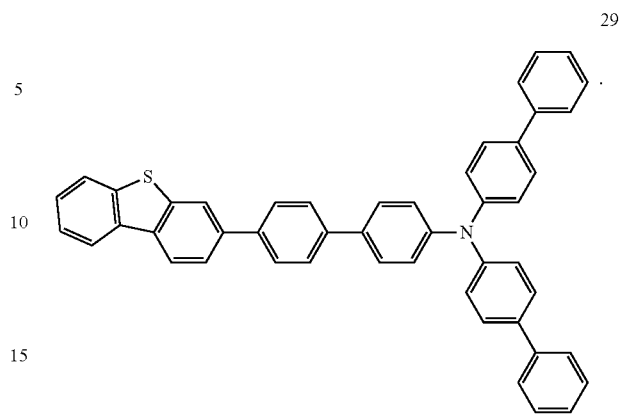
15. The organic EL device as claimed in claim 6, wherein the material for an organic EL device includes at least one of Compounds 33 to 42:
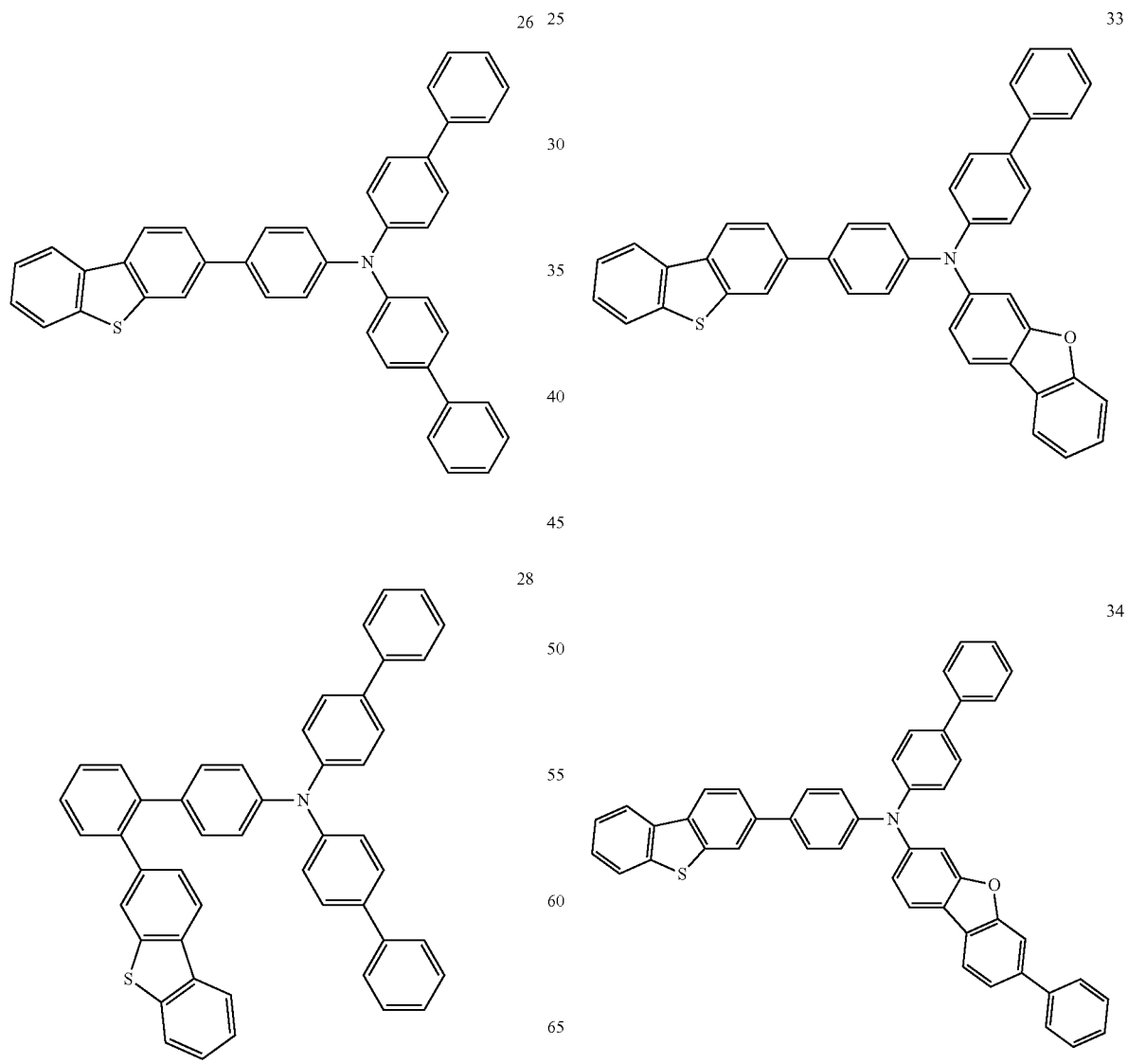

33
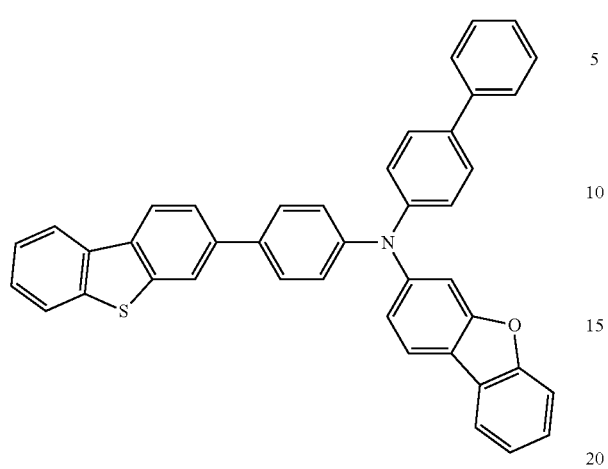
35
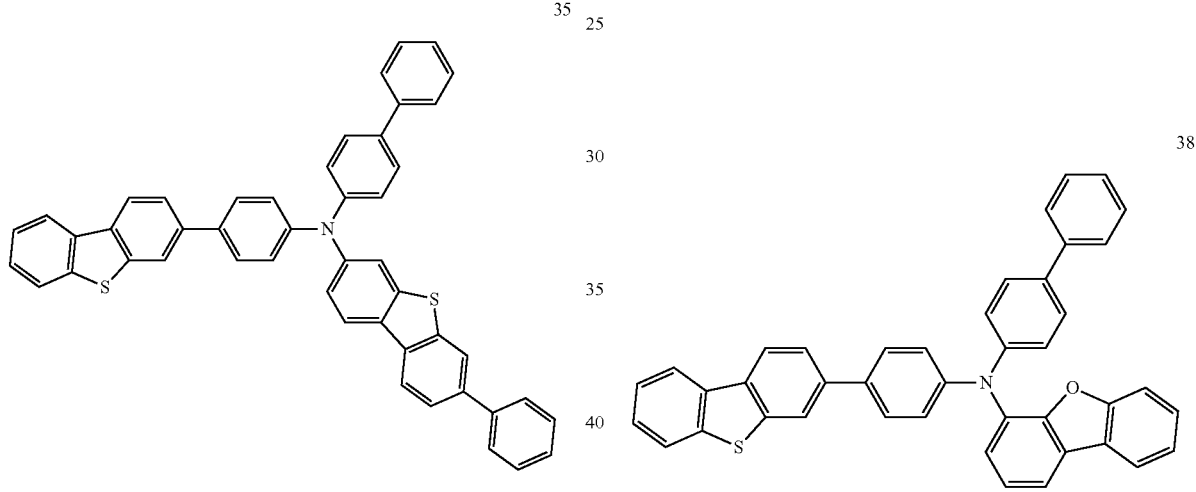
36
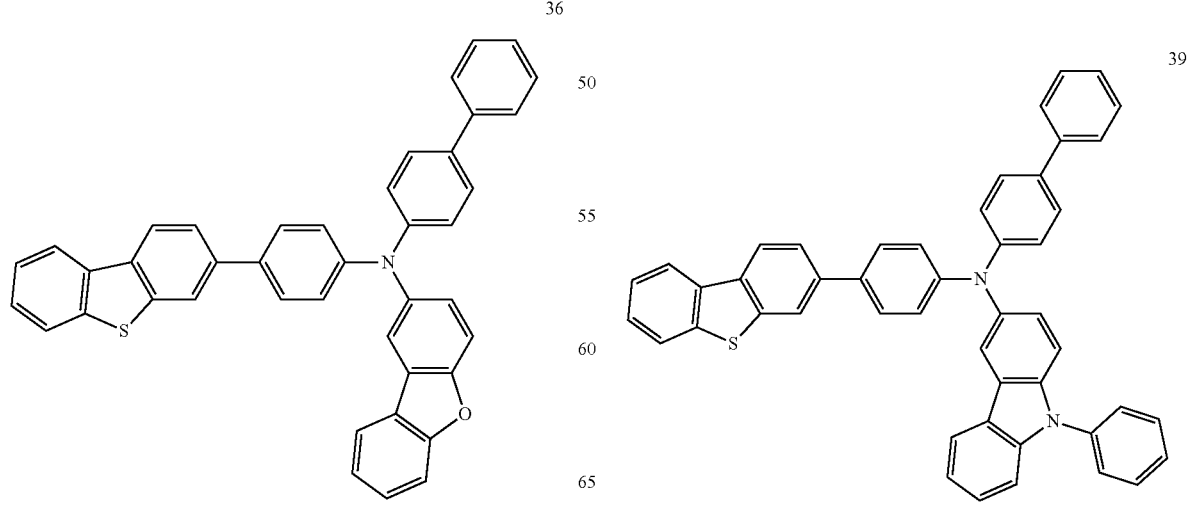
37
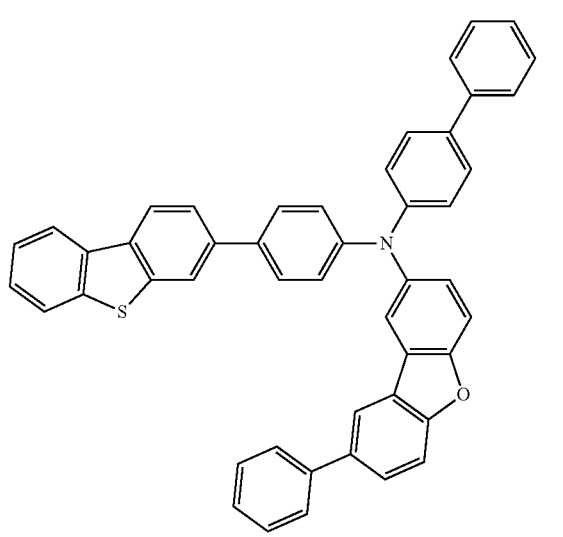
38
38
39

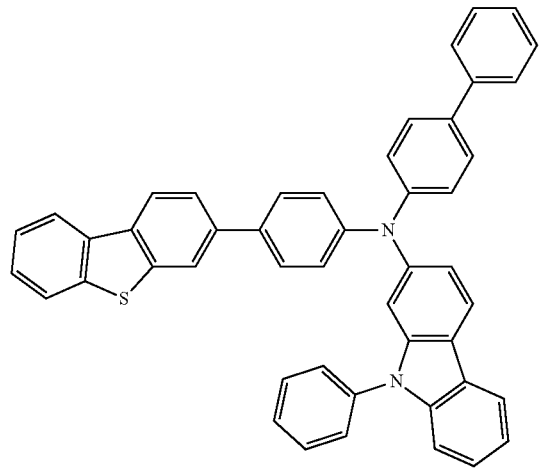
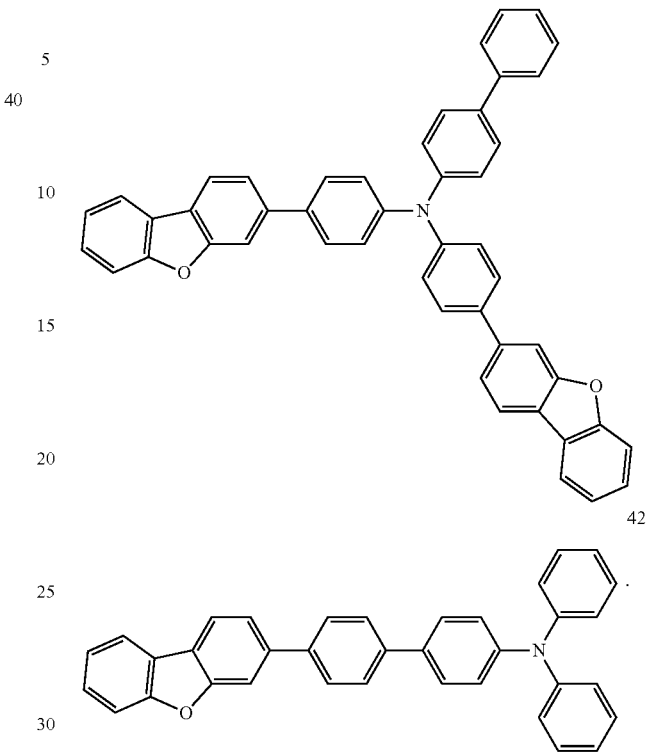
16. The organic EL device as claimed in claim 6, wherein the material for an organic EL device is included in a hole transport layer.
* * * * * United States Patent

EX PARTE REEXAMINATION CERTIFICATE (11627th)

United States Patent
Fuchiwaki

(10) Number: US 9,871,204 C1
(45) Certificate Issued: Jan. 16, 2020

(54) MATERIAL FOR ORGANIC ELECTROLUMINESCENCE DEVICE AND ORGANIC ELECTROLUMINESCENCE DEVICE USING THE SAME

(71) Applicant: SAMSUNG DISPLAY CO., LTD., Yongin, Gyeonggi-Do (KR)

(72) Inventor: Junta Fuchiwaki, Yokohama (JP)

(73) Assignee: SAMSUNG DISPLAY CO., LTD., Giheung-Gu, Yongin, Gyeonggi-Do (KR)

Reexamination Request:
No. 90/014,238, Nov. 30, 2018

Reexamination Certificate for:
Patent No.: 9,871,204
Issued: Jan. 16, 2018
Appl. No.: 14/570,394
Filed: Dec. 15, 2014

(30) Foreign Application Priority Data

Dec. 20, 2013 (JP) ................. 2013-264607

(51) Int. Cl.
*H01L 51/00* (2006.01)
*C07D 209/86* (2006.01)
*C07D 307/91* (2006.01)
*C07D 333/76* (2006.01)
*C09K 11/06* (2006.01)

(52) U.S. Cl.
CPC ........ *H01L 51/0061* (2013.01); *C07D 209/86* (2013.01); *C07D 307/91* (2013.01); *C07D 333/76* (2013.01); *C09K 11/06* (2013.01); *H01L 51/0072* (2013.01); *H01L 51/0073* (2013.01); *H01L 51/0074* (2013.01); *H01L 51/0058* (2013.01); *H01L 51/0081* (2013.01); *H01L 2251/308* (2013.01)

(58) Field of Classification Search
None
See application file for complete search history.

(56) References Cited

To view the complete listing of prior art documents cited during the proceeding for Reexamination Control Number 90/014,238, please refer to the USPTO's public Patent Application Information Retrieval (PAIR) system under the Display References tab.

*Primary Examiner* — Jerry D Johnson

(57) ABSTRACT

A material for an organic electroluminescence device is represented by the following Formula 1,

[Formula 1]

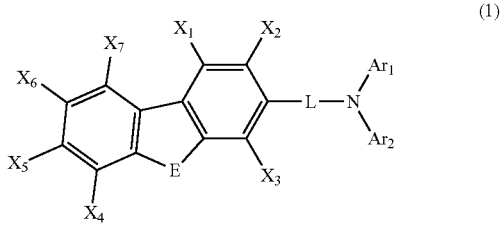

where $X_1$ to $X_7$, E, L, $Ar_1$ and $Ar_2$ are as defined in the specification.

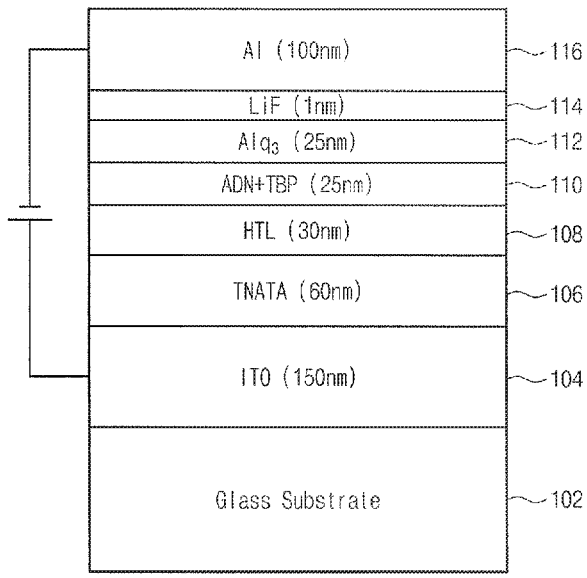

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 4, 6, 9 and 11 are cancelled.

Claims 1 and 10 are determined to be patentable as amended.

Claim 3, dependent on an amended claim, is determined to be patentable.

New claim 17 is added and determined to be patentable.

Claims 5, 7, 8 and 12-16 were not reexamined.

1. A material for an organic electroluminescence (EL) device represented by the following Formula 1:

[Formula 1]

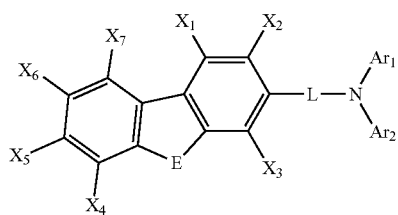
(1)

where $X_1$ to $X_7$ are each a hydrogen atom, $Ar_1$ [and $Ar_2$ are independently a substituted or] *is an* unsubstituted aryl group having 6 to 12 ring carbon atoms, or [a substituted or] *an* unsubstituted heteroaryl group having 5 to 13 ring carbon atoms *and $Ar_2$ is one of the following Groups (3) to (5)*:

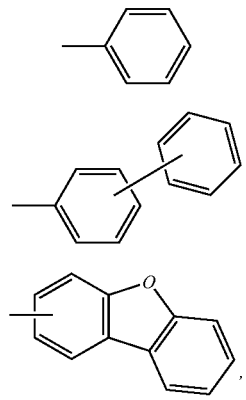

L is a divalent connecting group represented by the following Formula 2, n is 1 or 2, and E represents an oxygen atom or a sulfur atom,

[Formula 2]

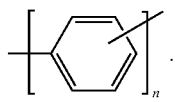
(2)

10. The organic EL device as claimed in claim [6] *17*, wherein E is an oxygen atom.

*17. An organic electroluminescence (EL) device, comprising a material for an organic EL device represented by the following Formula 6:*

*[Formula 6]*

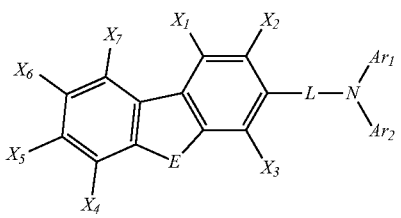
*(6)*

*where $X_1$ to $X_7$ are each a hydrogen atom,*

*$Ar_1$ is an unsubstituted aryl group having 6 to 12 ring carbon atoms, or an unsubstituted heteroaryl group having 5 to 13 ring carbon atoms and $Ar_2$ is one of the following Groups (3) to (5):*

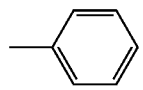
*(3)*

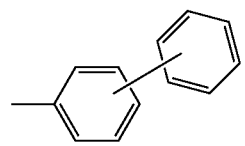
*(4)*

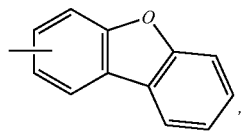
*(5)*

*L is a divalent connecting group represented by the following Formula 2,*

*n is 1 or 2, and*

*E represents an oxygen atom or a sulfur atom,*

*[Formula 2]*

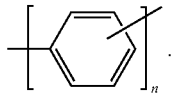
*(2)*

* * * * *